(12) United States Patent
Kowalczyk et al.

(10) Patent No.: US 9,965,584 B2
(45) Date of Patent: May 8, 2018

(54) IDENTIFYING INTERACTING DNA LOCI USING A CONTINGENCY TABLE, CLASSIFICATION RULES AND STATISTICAL SIGNIFICANCE

(75) Inventors: Adam Kowalczyk, Eveleigh (AU); Benjamin William Goudey, Eveleigh (AU); Eder Kikianty, Eveleigh (AU)

(73) Assignee: NATIONAL ICT AUSTRALIA LIMITED, Eveleigh, NSW (AU)

( * ) Notice: Subject to any disclaimer, the term of this patent is extended or adjusted under 35 U.S.C. 154(b) by 1046 days.

(21) Appl. No.: 14/118,352

(22) PCT Filed: May 17, 2012

(86) PCT No.: PCT/US2012/038319
§ 371 (c)(1),
(2), (4) Date: Mar. 17, 2014

(87) PCT Pub. No.: WO2012/158897
PCT Pub. Date: Nov. 22, 2012

(65) Prior Publication Data
US 2014/0214331 A1    Jul. 31, 2014

(30) Foreign Application Priority Data

May 17, 2011  (AU) ................................ 2011901881
Jun. 24, 2011  (AU) ................................ 2011902492

(51) Int. Cl.
*G06F 19/18*  (2011.01)
*G06F 19/24*  (2011.01)

(52) U.S. Cl.
CPC .............. *G06F 19/18* (2013.01); *G06F 19/24* (2013.01)

(58) Field of Classification Search
None
See application file for complete search history.

(56) References Cited

U.S. PATENT DOCUMENTS

| | | |
|---|---|---|
| 5,989,815 A | 11/1999 | Skolnick et al. |
| 7,058,517 B1 | 6/2006 | Denton et al. |
| 7,205,106 B1 | 4/2007 | Mirel et al. |
| 7,640,113 B2 | 12/2009 | Frudakis et al. |

(Continued)

FOREIGN PATENT DOCUMENTS

| | | |
|---|---|---|
| CN | 101880658 | 11/2010 |
| WO | 98/49887 | 11/1998 |
| WO | 2011/146056 | 11/2011 |

OTHER PUBLICATIONS

Chen et al., Comparative Analysis of Methods for Detecting Interacting Loci; 2011; 23 pages.

(Continued)

*Primary Examiner* — G. Steven Vanni

(57) ABSTRACT

A computer method of detecting interacting DNA loci by constructing a contingency table from samples of a first trait and samples of a second trait. The samples of the first and second trait are associated with one of a plurality of genotype calls, each relating to an interaction between multiple DNA loci. The contingency table includes frequencies of each genotype call in the samples. Based on the contingency table, measuring the association between the plurality of genotype calls and the first and second traits. Classifying the genotype calls into a first group that is statistically associated with the first trait and a second group that is statistically associated with the second trait.

21 Claims, 9 Drawing Sheets

(56) References Cited

U.S. PATENT DOCUMENTS

| | | |
|---|---|---|
| 7,729,864 B2 | 6/2010 | Schadt |
| 8,053,190 B2 | 11/2011 | Gorin et al. |
| 2002/0187496 A1 | 12/2002 | Andersson et al. |
| 2003/0224394 A1 | 12/2003 | Schadt et al. |
| 2005/0191731 A1 | 9/2005 | Judson et al. |
| 2005/0255504 A1 | 11/2005 | Parl |
| 2007/0005260 A1 | 1/2007 | Yokoyama et al. |
| 2007/0105146 A1 | 5/2007 | Mirel et al. |
| 2008/0009419 A1 | 1/2008 | Ralph et al. |
| 2010/0144538 A1 | 6/2010 | Belouchi et al. |
| 2010/0324943 A1 | 12/2010 | Klibanow |
| 2011/0098342 A1 | 4/2011 | Ramadass et al. |
| 2011/0112159 A1 | 5/2011 | Johnson |
| 2011/0287947 A1 | 11/2011 | Chen et al. |

OTHER PUBLICATIONS

Park et al., Penalized Logistic Regression for Detecting Gene Interactions; Apr. 2007; pp. 30-50.

Marchini et al., Genome-Wide Strategies for Detecting Multiple Loci that Influence Complex Diseases; Apr. 2005; pp. 413-417.

Moore et al., A Flexible Computational Framework for Detecting, Characterizing, and Interpreting Statistical Patterns of Epistasis in Genetic Studies of Human Disease Susceptibility; Feb. 2006; pp. 252-261.

Zhang et al., Bayesian Inference of Epistatic Interactions in Case-Control Studies; Sep. 2007; pp. 1167-1173.

M. Ritchie et al., Multifactor-Dimensionality Reduction Reveals High-Order Interactions Among Estrogen-Metabolism Genes in Sporadic Breast Cancer; Jun. 2001; pp. 138-147.

Brinza et al., RAPID detection of Gene-Gene Interactions in Genome-Wide Association of Studies; Sep. 2010; pp. 2856-2862.

H. Cordell, Epistasis: What it Means, What it Doesn't Mean, and Statistical Methods to Detect it in Humans; Jul. 2002; pp. 2463-2468.

Y. Liu et al., Genome-Wide Interaction-Based Association Analysis Identified Multiple New Susceptibility Loci Common Diseases; Mar. 2011; pp. 1-16.

H. Cordell, Detecting Gene-Gene Interactions that Underlie Human Diseases; Jun. 2009; 27 pages.

Chen et al., A Ground Truth Based Comparative Study on Detecting Epistatic SNPs; Nov. 2009; 15 pages, p. 26-31.

C. Yang et al., SNPHarvester: A Filtering-Based Approach for Detecting Epistatic Interactions in Genome-Wide Association Studies; 2009; pp. 504-511.

Park et al., "Penalized logistic regression for detecting gene interactions", Biostatistics (online), Epub Apr. 11, 2007, vol. 9, Issue 1, pp. 30-50.

Liu et al., "Genome-Wide Interaction-Based Association Analysis Identified Multiple New Susceptibility Loci for Common Diseases", PLoS Genetics (online), Mar. 17, 2011, vol. 7, Issue 3, pp. 1-16.

Chen et al., "Comparative analysis of methods for detecting interacting loci", BMC Genomics (online) Jul. 5, 2011, vol. 12, p. 344, pp. 1-23.

PCT International Search Report and Written Opinion of the International Searching Authority for PCT/US2012/038319, dated Aug. 3, 2012, 9 pages.

| Task (exhaustive search) | IG (<PLINK, MDR,...>) | BOOST (PC) | GBOOST (1GPU) | OPE-D (PC) | OPE-D (B/G) | OPE-D 1 GPU, once of $200 | OPE-D 200 GPU cloud, $200/h |
|---|---|---|---|---|---|---|---|
| | | | | | ~2,000PCs) $? | | |
| 300K, 2-way, SNP | 108d | 1.3d | 45min | 6h | <1min | 5min | <1min |
| 500K, 2-way, SNP | 300d | 3.5d | 2.1h | 17h | <1 min | 14min | <1min |
| 1M, 2-way, SNP | 3.3y | 13.9d | 8.3h | 2.8d | 2.0 min | 56min | <1min |
| 300K, 3-way, SNP | 29K y | 342y | 8.6y | 137y | 0.8 month | 1.9y | 83h ~3.5d~$17K |
| 500K, 3-way, SNP | 137K y | 1.5K y | 40y | 634y | 3.8 month | 8.8y | 390h ~16d |
| 1M, 3-way, SNP | 1,095K y | 12.6K y | 316y | 5K y | 30 month | 70.5y | 3100h~128d |

Fig. 8

IDENTIFYING INTERACTING DNA LOCI USING A CONTINGENCY TABLE, CLASSIFICATION RULES AND STATISTICAL SIGNIFICANCE

CROSS-RELATED APPLICATIONS

This present application claims priority from Australian Provisional Application Nos 2011902492 and 2011901881, the content of which is incorporated herein by reference.

TECHNICAL FIELD

This disclosure generally concerns bioinformatics, and in particular, a computer-implemented method for detecting interacting DNA loci. In another aspect, there is provided a computer system and computer program for performing the method.

BACKGROUND

During the last ten years a major development in the analysis of diseases and biological traits from a genetic viewpoint has been the introduction of Genome Wide Association studies (GWAS). A GWAS offers the ability to measure hundreds of thousands of genetic markers or single-nucleotide polymorphisms (SNPs) across the genome and provides a way to identify candidate genes related to a wide range of traits (for example, height, weight) and diseases (for example, breast cancer, asthma). Since 2005 alone, it is estimated that over 2,700 GWA studies have been conducted at an average cost of $500,000 per study. Given the high costs involved in running a GWAS, there is clearly a great need to ensure that the information in the collected data is fully utilised.

One of the main aims of GWAS is to identify DNA features which if not causal, are at least statistically significantly associated with increased risk of various diseases/traits or increased benefit from specific treatments. The single locus analysis approach used (predominantly) in analysis of these studies to date has yielded only modest results.

In order to overcome this roadblock, development of analysis techniques for detection of higher order interactions among DNA features is required. Higher order analysis of DNA interactions generally attracts the problem of having the numbers of features measured in genomic data, vastly exceeding the number of samples—the so called "curse of dimensionality", which requires development of new, powerful statistical and computational techniques.

SUMMARY

According to a first aspect, there is provided a computer-implemented method for detecting interacting DNA loci, the method comprising:
(a) constructing a contingency table from samples of a first trait and samples of a second trait,
    wherein the samples of the first trait and the samples of the second trait are each associated with one of a plurality of genotype calls each relating to an interaction between multiple DNA loci, and
    wherein the contingency table includes frequencies of each genotype call in the samples of the first trait and in the samples of the second trait;
(b) based on the contingency table, determining measures of association between the plurality of genotype calls, and the first trait or second trait; and
(c) using the measures of association and a binary classification rule, classifying the plurality of genotype calls into (i) a first group of genotype calls that is statistically significantly associated with the first trait, and (ii) a second group of genotype calls that is statistically significantly associated with the second trait.

The method binarises the problem of detecting interacting DNA loci and divides the genotype calls into two groups using the binary classification rule, i.e. statistically significantly associated with the first trait (e.g. disease) and statistically significantly associated with the second trait (e.g. being healthy). Advantageously, the method reduces the number of computations required and improving the efficiency of the detection. This is especially useful in practice where the method may be used on a large dataset, for example 500,000 single nucleotide polymorphisms (SNPs) may produce approximated 125 billion sets of SNP-pair. Further, since the samples are taken from a population at large, the one or more binary classification rules thereby quantify the statistical significance of the genotype calls being associated with the first trait or the second trait in the population.

Step (c) may comprise selecting the binary classification rule from multiple binary classification rules by:
    determining statistical significance of each of the multiple binary classification rules based on a statistical test on the measures of association, and
    selecting the binary classification rule that is most statistically significant in classifying the plurality of genotype calls.

The measures of association may include:
Ratio of proportion values, wherein each value is determined as a ratio between (i) a first proportion of samples of the first trait being associated with one of the genotype calls and (ii) a second proportion of samples of the second trait being associated with the genotype call. In this case, the statistical test may be a binomial margin test on the ratio of proportion values. In this case, selecting the binary classification rule to classify the plurality of genotype calls may further comprise reducing the number of the binary classification rules based on an ordering of the ratio of proportion values.
Difference of proportion values, wherein each value is determined as a difference between (i) a first proportion of samples of the first trait being associated with one of the genotype call and (ii) a second proportion of samples of the second trait being associated with the genotype call. In this case, statistical test may be a binomial margin test or maximum likelihood test on the difference of proportion values. In this case, selecting the binary classification rule to classify the plurality of genotype calls may further comprise reducing the number of the binary classification rules by grouping the genotype calls based on whether their difference of proportion values are negative or positive.

The method may further comprise: performing steps (a), (b) and (c) on multiple sets of DNA loci; ranking the sets of DNA loci according to statistical significance of their association with the (i) first trait or (ii) second trait; and based on the ranking, determine a list of sets of DNA loci that are most statistically significantly associated with the (i) first trait, or (ii) second trait.

Ranking the sets of DNA loci may be based on a gain in association of the DNA loci as a set with the (i) first trait, or (ii) second trait compared to individual association of each DNA locus in the set with (i) first trait, or (ii) second trait. One or more statistical tests may be performed on the sets of multiple DNA loci in the list to reduce the size of the list. The statistical test(s) may include one or more of logistic regression; chi-square test; and Fisher's exact test.

The method may further comprise providing a graphical interface that includes a visual representation that compares measures of association of plural sets of multiple DNA loci. An input interface may also be provided to receive input information relating to one or more statistical tests, and updating the visual representation according to the input information.

The method may further comprise profiling the samples to determine one or more attributes of the samples, and using the one or more attributes to determine the one or more binary classification rules in step (b). The attribute(s) may be related to one or more of: distribution of genotype calls across the samples of the first trait and the samples of the second trait; distribution of loci position; and distribution of statistics.

For verification purposes, the method may further comprise comparing genotype calls that are classified as statistically significantly associated with the first trait or second trait with data relating to the biological aspect of the samples. For example, the biological aspect may include association of the set of multiple DNA loci with a linkage-disequilibrium block to analyse interaction on linkage-disequilibrium block level; and/or a nearest gene to analyse interaction on gene level.

At least one of the plurality of genotype calls may relate to an interaction between multiple DNA loci, and at least one environmental variable.

The method may be used in many applications. For example, the first trait is resistance to a disease, and the second trait is lack of resistance to the disease; or the first trait is a resistance to a chemical, and the second trait is lack of resistance to the chemical; or the first trait is a response to a drug treatment, and the second trait is a lack of response to the drug treatment.

According to a second aspect, there is provided a computer program comprising executable instructions to cause a processing unit (including a processor, and a memory) to performing the method according to the first aspect.

According to a third aspect, there is provided a computer system for detecting interacting DNA loci associated with a disease or being healthy, the system comprising a processing unit to:
(a) construct a contingency table from samples of a first trait and samples of a second trait,
  wherein the samples of the first trait and the samples of the second trait are each associated with one of a plurality of genotype calls each relating to an interaction between multiple DNA loci, and
  wherein the contingency table includes frequencies of each genotype call in the samples of the first trait and in the samples of the second trait;
(b) based on the contingency table, determine measures of association between the genotype calls, and the first trait or second trait; and
(c) using the measures of association and a binary classification rule, classify the genotype calls into (i) a first group of genotype calls that are statistically significantly associated with the first trait, or (ii) a second group of genotype calls that are statistically significantly associated with the second trait.

BRIEF DESCRIPTION OF DRAWINGS

Non-limiting example(s) of the method and system will now be described with reference to the accompanying drawings, in which:

FIG. 4($b$) is a chart illustrating a binomial margin for difference of proportions;

FIG. 8 is a table comparing computational times of one example implementation of the method performed by the processing unit and other methods.

DETAILED DESCRIPTION

Figure 1:
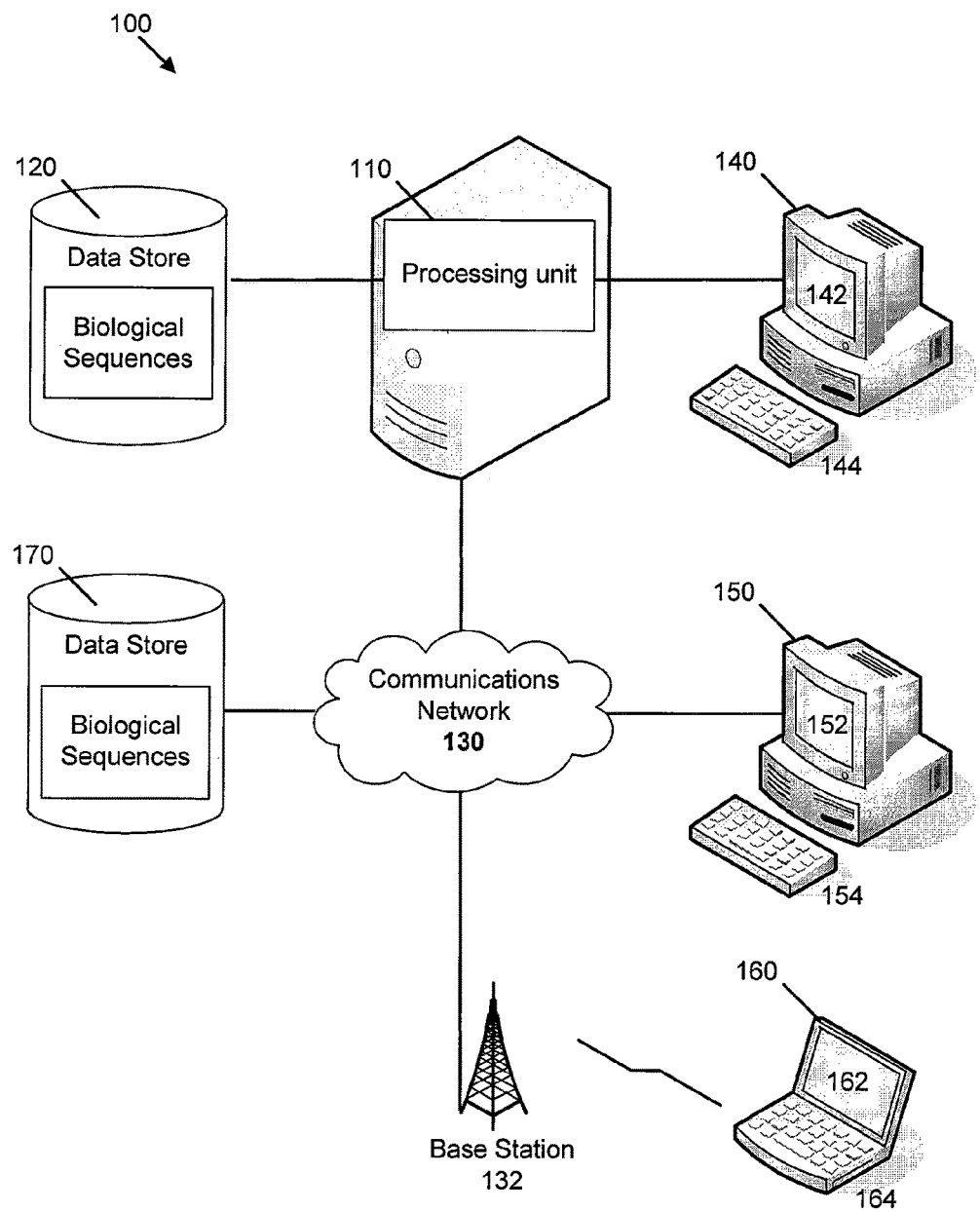
FIG. 1 is a schematic diagram of an example system for detecting interacting DNA loci.

Referring first to FIG. 1, a computer system 100 comprises a processing unit 110 and a local data store 120. The processing unit 110 is operable to implement a method for detecting interacting DNA loci.

A local computing device 140 controlled by a user (not shown for simplicity) can be used to operate the processing unit 110. The local computing device 140 is capable of receiving input data from a data entry device 144, and displaying output data using a display screen 142. Alternatively or in addition, the method can be offered as a web-based tool accessible by remote computing devices 150, 160 each having a display screen 152, 162 and data entry device 154, 164. In this case, the remote computing devices 150, 160 are capable of exchanging data with the processing unit 110 via a wide area communications network 130 such as the Internet and where applicable, a wireless communications network comprising a wireless base station 132. The remote computing devices 150, 160 may be any suitable devices, such as a laptop computer, hand-held mobile device, computer desktop, tablet computer, and personal digital assistant.

A DNA-loci interaction takes place when multiple mutations harboured by them interact to affect the risk associated with a disease or complex trait. Such an interaction could be manifested as an interaction of observables SNP-markers, which could sometimes be the causal mutations, but most likely are non-causal markers. In this way, some SNP markers with insignificant marginal effects may show relatively strong association to diseases or traits by interacting with other SNPs.

Epistasis, in biological terms, refers to the suppression or enhancement of expression of one gene by another. In statistical terms it generally refers to non-additive (i.e.

including non-linear) effect of two or more SNPs. Throughout this disclosure, we will use the term "epistasis" in a somewhat broader sense, including an additive effect, as this is also of prime interest and it is not easy to detect among the large number of possible combinations.

One example of the computer-implemented method for detecting interacting DNA loci performed by the processing unit 110 will now be described in more detail with reference to FIG. 2. The detection of interacting DNA loci is based on samples of a first trait and samples of a second trait that are each associated with one of a plurality of genotype calls each relating to an interaction between multiple DNA loci. A set of DNA loci might be two or more markers such as SNPs.

The method may be used in various applications. For example, the first and second traits may be, respectively, disease and healthy in human or animal; resistance to a chemical (e.g. pesticide in a plant) and lack of resistance to the chemical; response to a drug treatment or lack of response to a drug treatment. The genotype calls may also be each related to an interaction between multiple DNA loci, and at least one environment variable such as age, ethnicity, smoking or non-smoking, and body mass index (BMI).

Figure 2:
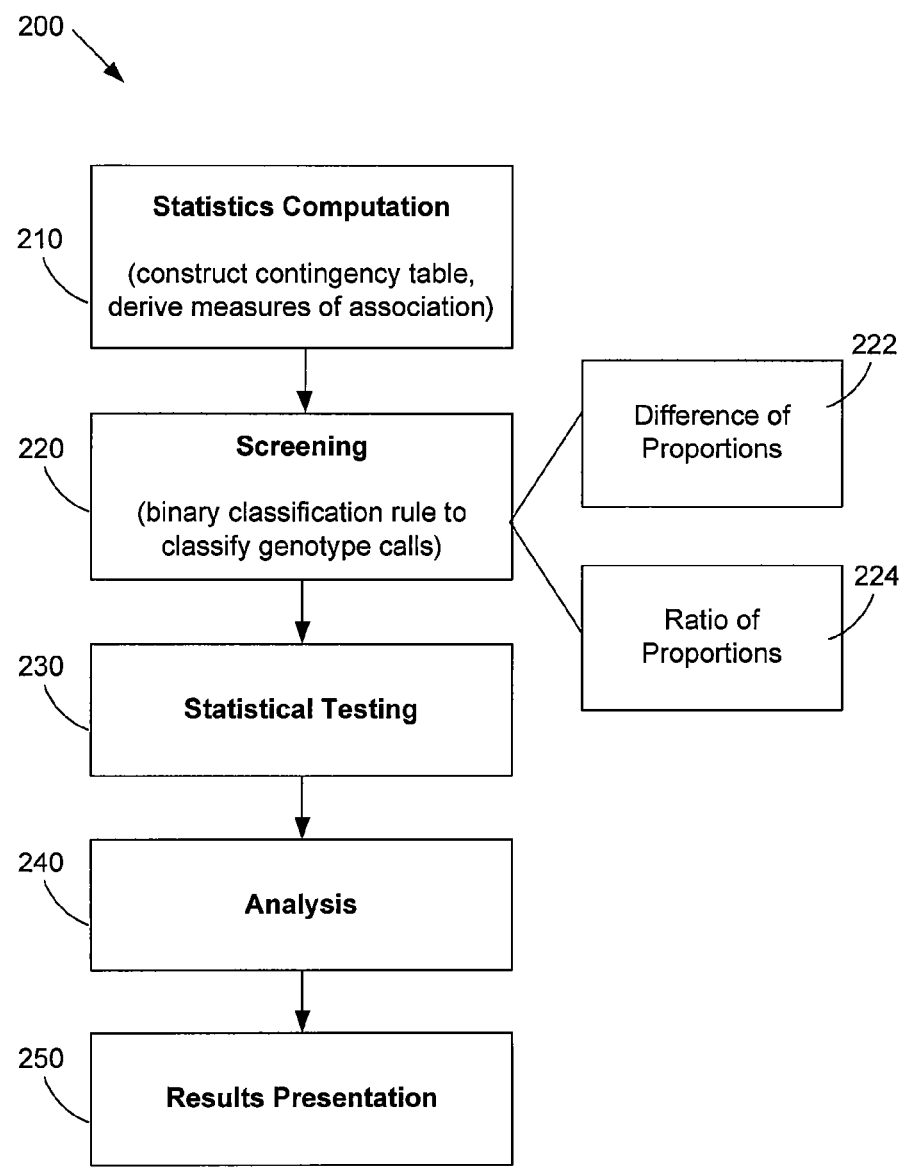
FIG. 2 is a flowchart of an example method performed by a processing unit for detecting interacting DNA loci.

In more detail, the example method in FIG. 2 comprises several stages of statistical filtering of potential candidates for epistasis.

Statistics Computation Stage 210

The processing unit 110 performs a statistics computation stage in which the necessary statistics required for subsequent steps are computed. This stage includes the development of statistical tables, which are data specific, and dependent on a number of cases and controls and, for some statistical tests, on other design parameters. A contingency table is first constructed from the samples, the table including frequencies of each genotype call in the samples of the first trait and in the samples of the second trait. Measures of association are also derived from the contingency table. Although the term "table" has been used here, it will be appreciated that any other suitable data structures (array, list etc.) may be used to store the contingency table in a memory, for example.

Screening Stage 220

The processing unit 110 screens trillions of candidate "sets of DNA loci" such as SNP-pairs and selects pairs (in order of millions) for further analysis. Using measures of association derivable from the contingency table and a binary classification rule, the processing unit 110 classifies the genotype calls into (i) a first group of genotype calls that is statistically significantly associated with the first trait, and (ii) a second group of genotype calls that is statistically significantly associated with the second trait. In other words, the genotype calls are split or divided into two groups. See also FIG. 3, in which a binary classification rule 310 is shown.

The measures of association may be ratio of proportions 224, difference of proportions 222, odds, odds ratio or any other suitable measures. In one example, difference of proportion values 222, wherein each value is determined as a difference between (i) a first proportion of samples of the first trait being associated with one of the genotype call and (ii) a second proportion of samples of the second trait being associated with the genotype call. The term "difference of proportions" will be used interchangeably with "difference of proportion values", "attributable risk" throughout this disclosure.

In another example, ratio of proportion values may be used, where each value is determined as a ratio between (i) a first proportion of samples of the first trait being associated with one of the genotype calls and (ii) a second proportion of samples of the second trait being associated with the genotype call. The term "ratio of proportions" will be used interchangeably with "ratio of proportion values", "risk ratio" and "relative risk" throughout this disclosure.

The binary classification rule may be selected or searched from multiple binary classification rules by, for example, determining statistical significance of each of the multiple binary classification rules based on a statistical test on the measures of association and selecting the binary classification rule that is most statistically significant in classifying the plurality of genotype calls. Prior to this, the number of the binary classification rules may be reduced to simplify the selection or search. The selected binary classification rule reflects the ability of the DNA loci to determine one of the traits. For example, the statistical test may be a binomial margin test on the ratio of proportion values 224 or difference of proportion values 222; or a binomial margin test or maximum likelihood test on the difference of proportion values 222.

In one implementation, the computation is maximally simplified, so a lot of information derived from the data may be dropped. In one implementation, the selected SNP-pairs are those who pass an acceptance criteria based on Bonferroni threshold.

Statistical Testing Stage 230

The processing unit 110 performs statistical testing on the selected SNP-pairs to further select SNP-pairs for additional analysis in step 240. This stage, for example, includes computing full contingency tables, evaluating statistics of the selected SNP-pairs, ranking the SNP-pairs such that most statistically significant pairs are selected for further analysis (i.e. to reduce the size of the list of pairs). For example, ranking the SNP-pairs may be based on a gain in association of the SNPs as a pair, compared with their individual association with the first trait or second trait. At this stage, the processing unit 110 may apply more computationally challenging filters (e.g. logistic regression) and cross check against results in alternative studies.

Analysis Stage 240

The processing unit 110 analyses the SNP-pairs that have passed previous rigorous statistical filtering stages for verification purposes. The analysis includes comparison with data relating to biological aspects of the samples. For example, the processing unit 110 may cross check for participation in specific biological processes or pathways with the intention of identifying underlying biology driving the interaction. This involves condensing the reported interacting loci to interacting regions (accounting for the effect of linkage-disequilibrium), mapping these regions to genomic features such as genes, and correlating these putative interacting genes with known biological interaction data such as protein-protein interactions or gene regulatory networks. Finally, identification of the causal SNP participating in the interaction is attempted.

Presentation Stage 250

The processing unit 110 presents the results on a suitable display screen 142, 152 and 162. The processing unit 110 provides a graphical interface that includes a visual representation that compares measures of association of plural sets of multiple DNA loci. For example, the results include an indication of interacting SNP-pairs that are associated with a trait (e.g. disease). The processing unit 110 also provides an input interface to receive input information relating to one or more statistical tests, and updating the visual representation according to the input information It will be appreciated that the method, in at least one embodiment, is based on proprietary statistical methods, which estimate the probability that an observation is due to "noise", and can therefore filter putative interactions that are significantly above the "noise". This is integrated with a computational procedure and further modified to optimise the speed of computation. The resulting algorithms show several orders of magnitude speed up over alternatives known to date, cutting the computational time from years to tens of minutes for exhaustive test for all pairs in modest size GWAS data.

Additionally in at least one embodiment, the method finds the maximal capability of every multi-locus tested to discriminate between considered phenotypes and ranks them according to a rigorously computed probability that the claimed results are observable in the general population. To the inventors' best knowledge, those features have not been reported in GWAS analysis to date. Furthermore, accuracy of the results may be checked via cross-checking with independent GWA studies of the same disease and comparison of results across simulated data.

More importantly, following the development of practicable and reliable methods for performing these higher dimensional searches, the results need to be made readily accessible to biomedical researchers, so they can be applied to translational studies of disease risk and treatment efficacy.

Non-limiting examples of stages 210 to 250 will now be described in more detail below. Although the method is illustrated using examples for detecting interacting DNA loci in the form of SNP-pairs, it will be appreciated that the method can be extended to detecting three or more interacting DNA loci. In some examples, disease (first trait) and healthy (second trait) samples are used to exemplify the method.

Statistics Computation Stage 210

This stage 210 involves development of statistical tables by the processing unit 110. The statistical tables are data specific and dependent on the number of cases and controls and, for some statistical tests, and on other design parameters.

The processing unit 110 uses two main classes of statistical tests, differing by the alternative hypothesis H1:
(a) Ratio of Risks (RoR) which quantifies the evidence for the RoR in the population is larger than a specified value $\rho_0$, possibly determined by the observed RoR, r.
(b) Difference of Risks (DoR), which quantifies the evidence for the DoR in the population is larger the a specified value $\delta_0$, possibly determined by the observed DoR, d.

It will be appreciated that the challenge is to find computable statistical tests which allow for rigorous evaluation of extreme tails of the distributions involved and have clear, direct link to the population parameters of interest. The ratio of risks (RoR), is generally a preferred scoring statistic for testing from the biological interpretation perspective. However, it cannot be tested directly (due to division by zero) and as such, necessitates the use two-dimensional distributions.

The different of risks (DoR) tests are easier from that perspective, being a well-defined one-dimensional statistics, but their tabulation requires more involved computations. The tests based on difference of risks facilitate efficient computational implementation and are used by the processing unit 110 in the screening stage 220, especially with Graphical Processing Unit (GPU) implementations. For that reason, they seem to be a natural choice for higher order interactions screening. They have a cost advantage over supercomputer implementation (e.g. IBM B/G P) of a factor 10 at least.

(a) Ratio of Risks (RoR)

Figure 3:
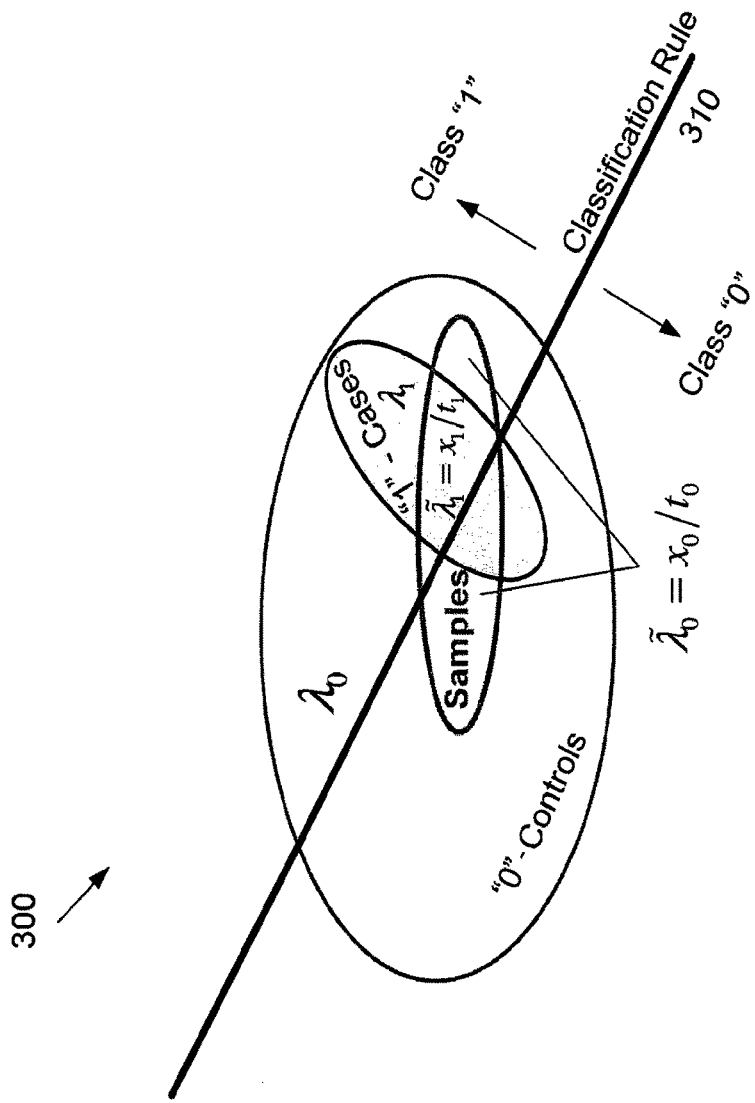
FIG. 3 is a schematic diagram illustrating populations of samples of a first trait (disease or "Cases") and samples of a second trait (healthy or "Controls"), and a binary classification rule.

Referring now to FIG. 3, consider two populations:
Population of diseased samples, $\mathbb{P}_0$, which is also denoted as "1" or "Cases";
Population of control or healthy samples, $\mathbb{P}_1$, which is also denoted as "0" or "Controls".

Each sample in the population has a particular allele of a specific binary genotype having a binary outcome, g: $\mathbb{P} \to \{0,1\}$. The proportion of g=1, or true relative risks in $\mathbb{P}_0$ and $\mathbb{P}_1$ are denoted $\lambda_0$ and $\lambda_1$, respectively. The proportion of a disease in a population is generally defined as the total number of cases of the disease in the population at a given time, divided by the number of cases in the population.

From the populations, subsets $\mathbb{S}_c \subset \mathbb{P}_c$ of $t_c$ elements are sampled, where c=0, 1. The random variable of counts of prevalence of g=1 in $\mathbb{S}_c$ is denoted as:

$$X_c := \{g(s)=1 | s \in \mathbb{S}_c\}.$$

Assuming the sample is small with respect to the population size, $X_c$ follows a binomial distribution, denoted here as $X_c \sim Bi(\lambda_i, t_i)$ having the following probability mass function:

$$P[X_c = x] = \binom{t_c}{x} \lambda_c^x (1-\lambda_c)^{t_c - x}$$

where x=0, 1, . . . , $t_c$ and c=0, 1.

For simplicity, let us consider a fixed pair of indices (a, b)$\in\{(0,1),(1,0)\}$ for the rest of the disclosure. Consider a particular sample $(\mathbb{S}_0, \mathbb{S}_1)$ and an observation of counts $(x_0, x_1)$ with the following ratio of risks:

$$r = \frac{x_b/t_b}{x_a/t_a} > 1.$$

The aim is to quantify the alternative hypothesis H1 that the true ratio of odds $\lambda_a/\lambda_b$ is larger than a specified value $\rho_0$, as represented as follows:

$$H1: \lambda_b/\lambda_a > \rho_0, \text{ where } 1 \leq \rho_0 \leq r.$$

In a typical hypothesis testing style, this is done by testing against the null hypothesis, which is in this case:

$$H0: \lambda_b/\lambda_a \leq \rho_0, \text{ where } 1 \leq \rho_0 \leq r.$$

Definition 1: Binomial Margin for Counts Test for Ratio of Risks (RoR)

The binomial margin for counts test for ratio of risks (RoR) that calculates the p-value for the null hypothesis H0 is therefore defined as $BMR_{\rho_0}{}^a C = BMR_{\rho_0}{}^a C(x_0, x_1; t_0, t_1)$:

$$BMR_{\rho_0}{}^a C(x_0, x_1; t_0, t_1) := \max_{\lambda_b/\lambda_a \leq \rho_0} P$$
$$[X_a \leq x_a \& X_b \leq x_b | X_c \sim B_i(\lambda_c, t_c), c=0,1]$$

Obviously, if condition $X_a \geq x_a \& X_b \leq x_b$ holds, then $$\frac{X_b/t_b}{X_a/t_a} \leq r.$$

As such, the ratio of risks test above finds the largest probability of observing counts $(X_0, X_1)$ generating the ratio of risks more extreme than r, for any selection of true relative risks $(\lambda_0, \lambda_1)$ satisfying the null hypothesis H0; see FIG. 4(a).

The "max" is used here to deal with the nuisance parameters, the unobservable true relative risks $(\lambda_0, \lambda_1)$. It enables computing of the rigorous upper bound. The computation of the binomial margin for counts test for ratio of risks (RoR) by the processing unit 110 involves a derivation of efficient numerical procedure and development of some technical solutions required to overcome issue caused by numerical over and under flows, caused by large values of sample sizes $t_a$ and $t_b$.

$$BMR_1^a C \leq BMR_{\rho_1}^a C \leq BMR_{\rho_0}^a C,$$

for $1 \leq \rho_1 \leq \rho_0$.

An example algorithm follows:

$$BMR_{\rho_0}^a C(x_0, , x_1 \mid t_0, t_1) =$$

$$\sum_{i=0}^{x_a} \binom{t_a}{i} \lambda_*^i (1-\lambda_*)^{t_a-i} \sum_{j=x_b}^{t_b} \binom{t_b}{j} (\rho_0 \lambda_*)^j (1-\rho_0 \lambda_*)^{t_b-j}.$$

where $\lambda_*$ is the unique solution of the following equation in open segment $(0, 1/\rho_0)$:

$$0 = -(t_a - x_a)\lambda \left[1 + \sum_{j=x_b+1}^{t_b} \prod_{k=x_b+1}^{j} \left(\frac{t_b - k + 1}{k}\right)\left(\frac{\rho_0 \lambda}{1 - \rho_0 \lambda}\right)\right] +$$

$$x_b(1-\lambda)\left[1 + \sum_{i=1}^{x_a} \prod_{k=1}^{j} \left(\frac{x_a - k + 1}{t_a - x_a + k}\right)\left(\frac{1-\lambda}{\lambda}\right)\right].$$

(b) Difference of Risks (DoR)

The concept of binomial margin for difference of risks, DoR, and some bounds for the p-values are described as follows.

Consider a particular observation of counts $(x_0, x_1)$ with the following empirical difference of risks:

$$d := \frac{x_b}{t_b} - \frac{x_a}{t_a} > 0$$

The aim is to quantify the validity of the following alternative hypothesis H1 that the difference of true ratio of risks is larger than a specified value $\delta_0$, $$H1: \lambda_b - \lambda_a > \delta_0$$

where $$\lambda_a = \frac{x_a}{t_a},$$

$$\lambda_b = \frac{x_b}{t_b}$$

are and $0 \leq \delta_0 \leq d$. As before, the corresponding null hypothesis is:

$$H0: \lambda_b - \lambda_a \leq \delta_0.$$

Definition 2: Binomial Margin for Difference of Risks (DoR)

The binomial margin for difference test for difference of risks (DoR) that calculates the p-value for the null hypothesis H0 is defined as $BMD_{\delta_0}^a D = BMD_{\delta_0}^a D(x_0, x_1; t_0, t_1)$:

$$BMD_{\delta_0}^a D(d; t_0, t_1) := \max_{\lambda_b - \lambda_a \leq \delta_0} P\left[\frac{X_b}{t_b} - \frac{X_a}{t_a} \geq d \mid X_c \sim Bi(\lambda_c, t_c), c = 0, 1\right],$$

The above test finds largest probability of observing counts $(X_0, X_1)$ generating the difference of risks more extreme than d, for any selection of true relative risks $(\lambda_0, \lambda_1)$ satisfying the null hypothesis H0.

In contrast to the ratio of risks test $BMR_{\rho_0}^a C$, the rigorous computation and tabulation of $BMD_{\delta_0}^a D$ is more difficult as it involves the explicit computation of computationally costly convolutions. However, there are relatively tight lower and upper bounds on it that are far easier to compute and have also a plausible interpretation as tests on the difference of risks on their own.

The lower bound of is given by:

$$\frac{x_b'}{t_b} - \frac{x_a'}{t_a} \geq d \Rightarrow P[X_a \leq x_a' \ \& \ x_b' \leq X_b] \leq P\left[\frac{X_b}{t_b} - \frac{X_a}{t_a} \geq d\right].$$

Computation of Difference of Risks

The following tight bounds allow for efficient computation (approximation) of the DoR in GWAS with thousands of samples, where issues to address are the numerical under and over flows cause by sample size to and $t_1$ in thousands. We have bounds:

$$\max_{x_b'/t_b - x_a'/t_a \geq d} \phi(x_a', x_b' \mid \delta_0) \leq$$

$$BMD_{\delta_0}^a D(x_0, x_1 \mid t_0, t_1) \leq \sum_{x'=0}^{\lfloor (1-d)t_a \rfloor} \phi(x', \lceil (\hat{d} + x'/t_a)t_b \rceil \mid \delta_0),$$

where $$\hat{d} := x_b/t_b - x_a/t_a$$

and $$\phi(x_a, x_b \mid \delta_0) = \binom{t_a}{x_a^\dagger}\binom{t_b}{x_b^\dagger}(p^*)^{x_a}(1-p^*)^{t_a - x_a^\dagger}(p^* + d)^{x_b^\dagger}(1 - p^* - d)^{t_b - x_b^\dagger} \times$$

$$\left(1 + \sum_{i=1}^{x_b^\dagger - x_b} g_i^- + \sum_{i=1}^{t_b - x_b^\dagger} g_i^+\right)\left(1 + \sum_{i=1}^{x_a^\dagger} f_i^- + \sum_{i=1}^{x_a - x_a^\dagger} f_i^+\right)\Bigg|_{p = p^*},$$

where $$x_a^\dagger := \min(x_a, \lfloor t_a p + 1 \rfloor),$$

$$f_0^\pm := 1, \quad f_i^\pm := f_{i-1}^\pm \left(\frac{(t_a - x_a^\dagger \mp i)p}{(x_a^\dagger \pm i)(1 - p)}\right)^{\pm 1}$$

for $i = 1, 2, \ldots,$ $$x_b^\dagger := \max(x_b, \lfloor t_b p + 1 \rfloor),$$

-continued $$g_0^\pm := 1, \quad g_i^\pm := g_{i-1}^\pm \left( \frac{(t_b - x_b^\dagger \mp i)(p+d)}{(x_b^\dagger \pm i)(1-p-d)} \right)^{\pm 1}$$

for 1, 2, ... , and p* is the unique solution of the following equation in the open segment $\max(0,-\delta_0)<p<\min(1-\delta_0,1)$:

$$\log\frac{(t_a - x_a^\dagger)!}{(t_a - x_a - 1)!} + \log\frac{(x_b - 1)!}{x_b^\dagger!} - \log\frac{x_a!}{x_a^\dagger!} - \log\frac{(t_b - x_b^\dagger)!}{(t_b - x_b)!} =$$

$$-\log\left(1 + \sum_{i=1}^{x_b^\dagger - x_b} g_i^- + \sum_{i=1}^{t_b - x_b^\dagger} g_i^+\right) - (x_b - x_b^\dagger)\log\left(\frac{1}{p+d} - 1\right) +$$

$$\log\left(1 + \sum_{i=1}^{x_a^\dagger} f_i^- + \sum_{i=1}^{x_a - x_a^\dagger} f_i^+\right) + (x_a - x_a^\dagger)\log\left(\frac{1}{p} - 1\right) + \log\frac{1-p}{p+d}.$$

All terms $g_i^\pm$ and $f_i^\pm$ under the sums are decreasing monotonically form 1 towards 0 for every $\max(0,-\delta_0) <p<\min(1-\delta_{0,1})$.

Definition 3: Binomial Margin Count-Difference Test for Difference of Risks (DoR)

The binomial margin count-difference test for difference of risks (DoR) is therefore defined as $BMD_{\delta_0}{}^a CD = BMD_{\delta_0}{}^a CD(x_0,x_1;t_0,t_1)$:

$$BMR_{\delta_0}^a CD(x_0, x_1; t_0, t_1) :=$$

$$\max_{x_0', x_1' : \frac{x_b'}{t_b} - \frac{x_a'}{t_a} \geq \frac{x_b}{t_b} - \frac{x_a}{t_a}} \max_{\lambda_b - \lambda_a \leq \delta_0} P[X_a \leq x_a' \,\&\, x_b' \leq X_b].$$

where "max" is over all feasible counts $(x'_0, x'_1)$ such that $$\frac{x_b'}{t_b} - \frac{x_a'}{t_a} \geq \frac{x_b}{t_b} - \frac{x_a}{t_a};$$

see corresponding illustration in FIG. 4(b). The counts-ratio test makes the lower bound for $BMR_{\delta_0}{}^a D$ defined in Definition 2, that is:

$$BMD_{\delta_0}{}^a CD(x_0,x_1;t_0,t_1) \leq BMD_{\delta_0}{}^a D(x_0,x_1;t_0,t_1).$$

Note that:

$$BMD_0{}^a CD \leq BMD_{\delta_0}{}^a CD \leq BMD_{\delta_0}{}^a CD,$$

for $1 \leq \delta_1 \leq \delta_0$. In the special case of $\delta_0 = 0$, the binomial margin for ratio defined in Definition 1 could be utilised.

$$BMR_0^a CD(x_0, x_1; t_0, t_1) := \max_{x_0', x_1' : \frac{x_b'}{t_b} - \frac{x_a'}{t_a} \geq \frac{x_b}{t_b} - \frac{x_a}{t_a}} BMR_1^a C(x_0', x_1'; t_0, t_1).$$

Definition 4: Maximum Likelihood Test for Difference of Risks

Let $$\psi = (x_0', x_1', p) := \binom{t_a}{x_a} \lambda^{x_a'}(1-\lambda)^{t_a - x_a'} \binom{t_b}{x_b'} (\lambda + \delta)^{x_b'}(1-\lambda-\delta)^{t_b - x_b}$$

for any integers $(x'_a, x'_b) \in [0, t_a] \times [0, t_b]$ and $0 \leq \lambda \leq 1$. Let $\lambda_* = \lambda_*(x'_a, x'_b)$ denote that real root of the following cubic equation in $\lambda$ $$0 = \lambda^3(t_a + t_b) + \lambda^2[d(t_b + 2t_a) - t_a - t_b - x_a' - x_b'] +$$
$$\lambda[x_a' + x_b' - d(t_a + t_b + 2x_a') + d^2 t_a] + d(1-d)x_a'\big|_{d = x_b'/t_b - x_a'/t_a}$$

which maximizes the function $\lambda \mapsto \psi(x', x'', \lambda)$; this root is chosen out of maximally three possibilities.

The maximum likelihood difference test for DoR is defined as follows:

$$mlBMD_{\delta_0}^a D(x_0, x_1; t_0, t_1) := \sum_{x_0', x_1'} \psi_a(x_0', x_1'; \lambda_*(x_0', x_1'))$$

where the sum is over all integers $0 \leq x'c \leq t_c$, $c=0,1$ such that $$\frac{x_b'}{t_b} - \frac{x_a'}{t_a} \geq d := \frac{x_b}{t_b} - \frac{x_a}{t_a}$$

and $\lambda_*(x'_0, x'_1)$ is the root of the cubic equation as defined above.

This test is relatively easy to compute, but care must be taken in computation of the sum due to the potential underflows.

Definitions 2 and 3 yield the upper and lower bounds of $BMD_{\delta_0}{}^a D$ defined in Definition 2 can be summarised as follows:

$$BMD_{\delta_0}{}^a CD \leq BMD_{\delta_0}{}^a D \leq mlBMD_{\delta_0}{}^a D.$$

Screening Stage 220

Referring to FIG. 2 again, the processing unit 110 then proceeds to analyse candidate SNP-pairs using binary classification rules to select SNP-pairs that are statistically significant. As will be explained below, the binary classification rules relates to the ratio of risks or difference of risks associated with the candidate SNP-pairs.

It will be appreciated that this stage is the most critical and computationally intensive out of all the stages. It involves checking all pairs of loci (typically trillions) and prioritizing interactions for further analysis (a reduction to millions of reported interactions), carried out by processing unit 110. The computation is maximally simplified by a reduction in the interactions reported, by only reporting the identities of the SNP-pairs which pass an acceptance criteria, e.g. based on Bonferroni threshold on the statistical significance of the interaction with respect to "noise" or an improvement of pair over individual SNPs measured by decrease in associated p-values.

Binary Genotype

The genotype call of a single SNP can have three proper values, denoted here as g=0, 1 or 2 for the majority homogenous (e.g. "AA"), heterogeneous (e.g. "Aa") and minority homogeneous (e.g. "aa") calls, respectively, or be missing, denoted as g=⊕. As such, the genotype calls for a pair of SNPs have 10 values as follows:

$$\text{Genotype call, } g = \begin{cases} 0 & \text{where } 0 \equiv {}'00' \\ 1 & \text{where } 1 \equiv {}'01' \\ 2 & \text{where } 2 \equiv {}'02' \\ 3 & \text{where } 3 \equiv {}'10' \\ 4 & \text{where } 4 \equiv {}'11' \\ 5 & \text{where } 5 \equiv {}'12' \\ 6 & \text{where } 6 \equiv {}'20' \\ 7 & \text{where } 7 \equiv {}'21' \\ 8 & \text{where } 8 \equiv {}'22' \\ 9 & \text{where } 9 \equiv {}'\oplus' \end{cases}$$

The first 9 values (0 to 8) are proper values each being a combination of 3 proper singleton calls. The 10th value indicates that one of the singleton calls is missing. The "missing" means here the genotype call could not been determined for a particular samples due to technical reasons, e.g. a fault in the microarray used.

Contingency Tables

The properties of a single SNP for determination of the phenotype can be encapsulated in a 2×4=2×(3+1) contingency table which for a pair of SNPs proliferates to the 2×10=2×(3×3+1) contingency table; see Tables 1.1 to 1.3 below. Analogously, in the case of triplet of SNP (three SNPs), the contingency table is 2×28=2×(3×3×3+1).

TABLE 1.1

Contingency Table (2 × 3 + 1) of counts for SNP v'

| | SNP v' | | | | |
|---|---|---|---|---|---|
| | 0 | 1 | 2 | ⊕ | |
| Control = 0 | $n'_{00}$ | $n'_{01}$ | $n'_{02}$ | $n'_{0\oplus}$ | $n'_0$ |
| Case = 1 | $n'_{10}$ | $n'_{11}$ | $n'_{12}$ | $n'_{1\oplus}$ | $n'_1$ |
| | $n'_{\Sigma 0}$ | $n'_{\Sigma 1}$ | $n'_{\Sigma 2}$ | $n'_\oplus$ | $n$ |

TABLE 1.2

Contingency Table (2 × 3 + 1) of counts for SNP v''

| | SNP v'' | | | | |
|---|---|---|---|---|---|
| | 0 | 1 | 2 | ⊕ | |
| Control = 0 | $n''_{00}$ | $n''_{01}$ | $n''_{02}$ | $n''_{0\oplus}$ | $n''_0$ |
| Case = 1 | $n''_{10}$ | $n''_{11}$ | $n''_{12}$ | $n''_{1\oplus}$ | $n''_1$ |
| | $n''_{\Sigma 0}$ | $n''_{\Sigma 1}$ | $n''_{\Sigma 2}$ | $n''_\oplus$ | $n''$ |

TABLE 1.3

Contingency Table 2 × (3 × 3 + 1) of counts for SNP-pair (v', v'')

| | | SNP v' | | | | |
|---|---|---|---|---|---|---|
| | | 0 | 1 | 2 | ⊕ | |
| Control (0) | | | | | | |
| SNP v'' | 0 | $n_{000}$ | $n_{001}$ | $n_{002}$ | $n_{00\oplus}$ | $n_{00\Sigma}$ |
| | 1 | $n_{010}$ | $n_{011}$ | $n_{012}$ | $n_{01\oplus}$ | $n_{01\Sigma}$ |
| | 2 | $n_{020}$ | $n_{021}$ | $n_{022}$ | $n_{02\oplus}$ | $n_{02\Sigma}$ |
| | ⊕ | $n_{0\oplus 0}$ | $n_{0\oplus 1}$ | $n_{0\oplus 2}$ | $n_{0\oplus\oplus}$ | $n_{0\oplus}$ |
| | | $n_{0\Sigma 0}$ | $n_{0\Sigma 1}$ | $n_{0\Sigma 2}$ | $n_{0\Sigma\oplus}$ | $n_0$ |

TABLE 1.3-continued

Contingency Table 2 × (3 × 3 + 1) of counts for SNP-pair (v', v'')

| | | SNP v' | | | | |
|---|---|---|---|---|---|---|
| | | 0 | 1 | 2 | ⊕ | |
| Case (1) | | | | | | |
| SNP v'' | 0 | $n_{100}$ | $n_{101}$ | $n_{102}$ | $n_{10\oplus}$ | $n_{10\Sigma}$ |
| | 1 | $n_{110}$ | $n_{111}$ | $n_{112}$ | $n_{11\oplus}$ | $n_{11\Sigma}$ |
| | 2 | $n_{120}$ | $n_{121}$ | $n_{122}$ | $n_{12\oplus}$ | $n_{12\Sigma}$ |
| | ⊕ | $n_{1\oplus 0}$ | $n_{1\oplus 1}$ | $n_{1\oplus 2}$ | $n_{1\oplus\oplus}$ | $n_{1\oplus}$ |
| | | $n_{1\Sigma 0}$ | $n_{1\Sigma 1}$ | $n_{1\Sigma 2}$ | $n_{1\Sigma\oplus}$ | $n_1$ |

For difference of risks, a 1×(3+1) contingency table is required for a single SNP (no interaction) and a (3×3+1) contingency table is required for an SNP-pair; see below.

TABLE 2.1

Contingency Table 1 × (3 + 1) for difference of risks for SNP v'
SNP v'

| 0 | 1 | 2 | ⊕ |
|---|---|---|---|
| $d'_0$ | $d'_1$ | $d'_2$ | |

TABLE 2.2

Contingency Table 1 × (3 + 1) for difference of risks for SNP v''
SNP v''

| 0 | 1 | 2 | ⊕ |
|---|---|---|---|
| $d''_0$ | $d''_1$ | $d''_2$ | |

TABLE 2.3

Contingency Table (3 × 3 + 1) for difference of risk: for SNPs v' and v''

| | | SNP v' | | | |
|---|---|---|---|---|---|
| | | 0 | 1 | 2 | ⊕ |
| SNP v'' | 0 | $d_{00}$ | $d_{01}$ | $d_{02}$ | $d_{0\Sigma}$ |
| | 1 | $d_{10}$ | $d_{11}$ | $d_{12}$ | $d_{1\Sigma}$ |
| | 2 | $d_{20}$ | $d_{21}$ | $d_{22}$ | $d_{2\Sigma}$ |
| | ⊕ | | | | $d_{\oplus\Sigma}$ |
| | | $d_{\Sigma 0}$ | $d_{\Sigma 1}$ | $d_{\Sigma 2}$ | $d_{\Sigma\oplus}$ | 0 |

Binary Classification Rule

Consider a genotype g with |V| proper values, $V=\{v_i\}_{0 \leq i \leq |V|} = \{0, 1, \ldots, |V|-1\}$ or g=⊕ if the call is missing. A binary classification or decision rule, $f: V \rightarrow \{0,1\}$ additionally defines as $f(\oplus)=\oplus$ for the missing call; see also 310 in FIG. 3. The binary genotype is defined as superposition of both functions into the space:

$$f \circ g : \mathbb{P} \rightarrow \{0, 1, \oplus\}$$

The binary genotype maps the population $\mathbb{P}$ and the space of samples $\mathbb{S}$, in particular. This is uniquely determined by the subset $V_1 \subset V$ of all proper genotype values which are mapped to 1. In other words, the binary classification rule classifies or divides the genotype calls into two subsets or groups, either statistically significantly associated with a first trait (e.g. disease) or statistically significantly associated with a second trait (e.g. healthy).

As such, there are $2^{|V|}$ different binary genotypes in total and half of this is the number of the linked binary genotype pairs, related by the logical complement, i.e. by the swap between 0 and 1 values. This implies that there are $2^3=8$ for a single SNP, $2^9=512$ for an SNP-pair and $2^{27}=1.34 \times 10^8$ for an SNP-triplet for the different binary genotypes possible.

Referring to FIG. 3 again, an ideal classification rule is one that separates all "Cases" (first trait—disease samples) from all "Controls" (second trait—healthy samples). Thus, an ideal rule has a 100% genotype frequency in "Cases", i.e. allocating 'yes' for all "Cases" and an infinite ratio of risks for genotype for "Cases" to risks for "Controls". For an imperfect rule, the quantification of "quality" is more complex: it depends on the balance between both ratio of risks and frequencies of genotype.

A number of statistics can be derived to implement this balancing, and in at least one embodiment of the method, p-values are used to quantify the ability of the rule to determine its performance in the population on the basis of classification of available sample data.

Optimal Binary Genotype

The processing unit 110 applies the binomial margin tests explained in the previous section to the candidate SNP-pairs. The binomial margin test is denoted as:

$$BM(x_0, x_1; t_0, t_1) = \begin{cases} BMR_{\rho_0}^a C(x_0, x_1; t_0, t_1) & \text{for Relative Risk} \\ BMD_{\delta_0}^a D(x_0, x_1; t_0, t_1) & \text{for Difference of Risks} \end{cases}$$

where:

$x_0$ and $x_1$ represent the observed counts in the "Control" and "Cases" samples respectively;

$t_0$ and $t_1$ represent the total number of counts in the "Control" and "Cases" samples respectively;

$BMR_{\rho_0}^a C(x_0, x_1; t_0, t_1)$ represents the test defined in Definition 1; and $BMD_{\delta_0}^a D(x_0, x_1; t_0, t_1)$ represents the test defined in Definition 2.

The optimal p-value of $BM(x_0, x_1; t_0, t_1)$ can be calculated as:

$$BM_*(g|S_0, S_1) = \min_f BM(x_0, x_1; t_0, t_1)|_{x_c = |\{s \in S_c | f \circ g(s) = 1\}|}$$

for c=0, 1.

The exhaustive search for $f$ through all possible cases off is impractical in the case of SNP pairs or triplets. Here are $2^{|V|}$ possible $f$ which are $2^9=512$ if $|V|=3^2$ and $2^{27}=1.3 \times 10^8$ if $|V|=27=3^3$ for a triplet of SNPs. However, there is a simple procedure which solves this problem efficiently under assumption that BM is extendible to a function on an open subset of $[0,1]^2$ with convex super-levels, i.e. such that the following sets are convex, $$\{(x_0, x_1) | BM(x_0, x_1; t_0, t_1) \geq \theta\} \subset \mathbb{R}^2$$

for all $\theta \leq \theta_0$ where $\theta_0 \in \mathbb{R}$ is a constant.

Let's denote the number of genotype call g=v in the set $\mathbb{S}^c$ by $$|g^{-1}(v|\mathbb{S}_c| := |\{s \in \mathbb{S}_c | g() = v\}|$$

for c=1,2 and the sample RoR with phenotype $\alpha \in \{0,1\}$ as the reference by $$RoR^a(v|g) := \frac{|g^{-1}(v|S_b)|}{|g^{-1}(v|S_a)|}.$$

Let $v(\tau)$ for $\tau = 0, 1, \ldots, |V|-1$ be an ordering of values of genotype g such that the function $\tau \mapsto RoR^a(v_\tau|g)$ is descending. It can be proven formally that the optimal binary genotype function $f_*$ is given by the following:

$$BM_*(g) = \min_\tau BM(x_0, x_1; t_0, t_1)|_{x_c = \Sigma_{j=0}^\tau |g^{-1}(v_\tau|S_c)|}$$

for c=0, 1. In this case, the subset of genotype calls defining optimal binary genotype function $f_*$ is $V_1 := \{v_0, v_1, \ldots, v_{\tau_*}\}$, where $\tau_*$ is the argument of the minimum above. It will be appreciated that the determination of optimal binary genotype $f_*$ is model free, i.e. does not involve any prior assumptions of the form of the binary function. This is a major simplification in the search for optimality.

It will be appreciated that the above result can be formulated for the discrete case, without an assumption of extendibility to convex function on the continuous domain. We shall present those results elsewhere. Here we are satisfied with the use of heuristics suggested by the above theorem, as it is sufficient for detection of significant interactions. Would have the above result been not fully applicable to our discrete case, the list of significant interactions would have been under reported, in which case there will be some false negative. This has minimal impact on the overall algorithm which seem to produce a large number of significant calls.

Figure 4:
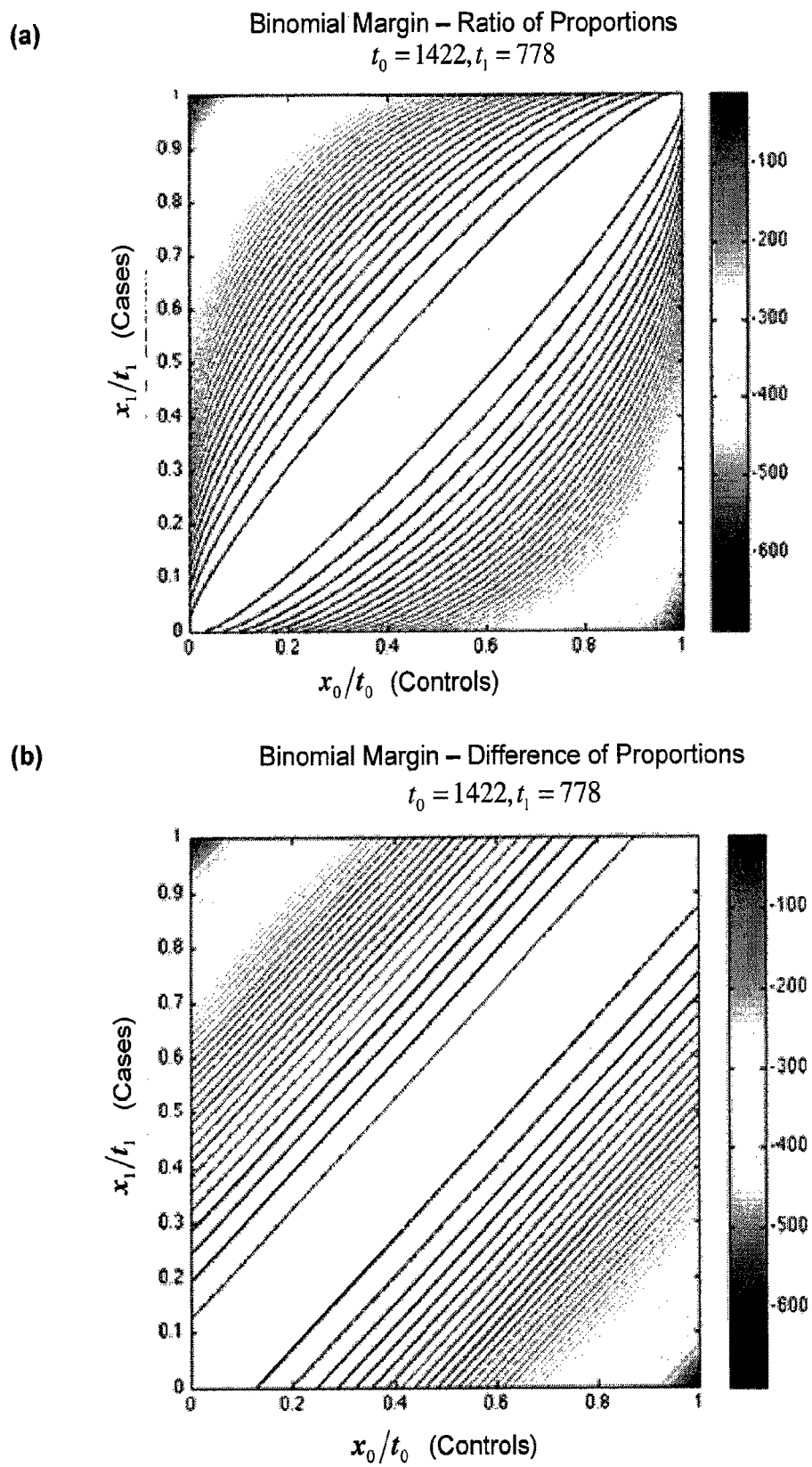
FIG. 4($a$) is a chart illustrating a binomial margin for ratio of proportions.

A visual inspection of plots in FIG. 4 shows that the super-level curves of log 10 of p-values for $BMR_{\rho_0}^a C$, $BMD_{\delta_0}^a CD$ and $mlBMD_{\delta_0}^a D$ are convex, once the roughness due to their discreteness is "smoothed out".

In other words, the binary classification rule that splits the genotype calls into two groups is selected from multiple binary classification rules based on a statistical test on the measures of association. Two example algorithms are presented below: (i) Algorithm 1 based on difference of risks, or (i) Algorithm 2 based on ratio of risks.

Algorithm 1: Screening for Optimal Difference of Risks

The binary classification rules may be related to differences of risks derived from the contingency table. In this case, the screening algorithm performed by the processing unit 110 evaluates the maximal difference of risks, and remove all SNP-pairs that do not satisfy a predefined threshold, which is exemplified using Bonferroni threshold, $D_{Bonf}$.

| | |
|---|---|
| Given: | |
| | Two genotyping matrices $[x_{a,l}]$, $s \in \mathbb{S} := \{1, 2, \ldots, n\}$ and $l \in \mathcal{L} := \{1, 2, \ldots, m\}$, with integer values in $V := \{0, 1, \ldots, |V|-1\}$. |
| | The split of samples $\mathbb{S}$ into two non-empty genotype subsets, $\mathbb{S}_1$ of $n_1$ "cases" and $n_0 := n - n_1$ "controls", $\mathbb{S}_0 := \mathbb{S} \setminus \mathbb{S}_1$. |
| | The minimal value of odds difference, $D_{Bonf}$ ($\equiv$ Bonferroni correction) is defined as a number such that $BMA_0^a(D_{Bonf}) - 1/(2^m)$ |
| | A level of improvement $\Delta > 0$. Initialise: |
| 1. | $C := n_1/n_0$; |
| 2.0 | For every locus $l \in \mathcal{L}$, find the ODR, D(l): |
| | Initialise: D(l) = 0, d(l, 0) = 0 and $d_0 = 0$, then |
| 2.1 | for every non-zero value $v \in V \setminus 0$ evaluate: |

```
2.2             d(l, v) := ∑_{s∈S_1} 𝒥[x_{a_sl} ≡ v] − C ∑_{s∈S_0} 𝒥[x_{a_sl} ≡ v], 2.3             D(l) = D(l) + max{0, d(l, v)};
2.3             d(l, 0) = d(l, 0) − d(l, v);
2.5          end
2.6          D(l) = D(l) + max{0, D(l, 0)};
2.7       end
3.0       For every pair of loci (l', l'') ∈ 𝓛 × 𝓛:
3.1          Compute compute ODR, D = D(l', l''):
3.2          Initialise D = 0, d_{00} = d''(l'', 0), d_{v'0} = d'(l', v') and d_{0v''} = d''(l'', v'') for
                (v', v'') ∈ (V\0) × (V\0);
3.3          For every pair of non-zero values (v', v'') ∈ (V\0) × (V\0) evaluate:

3.4             d = ∑_{s∈S_1} 𝒥[x'_{sl'} ≡ v' & x''_{al''} ≡ v''] − C ∑_{s∈S_0} 𝒥[x'_{sl'} ≡ v' & x''_{sl''} ≡ v''], 3.5             D = D + max{0, d};
3.6             d_{v'0} = d_{v'0} − d;
3.7             d_{0v''} = d_{0v''} − d;
3.8          end;
3.9          For every v = V\0 evaluate:
3.10            D = D + max{0, d_{v0}};
3.11            d_{00} = d_{00} − d_{v0};
3.12         end;
3.13         D = D + max{0, d_{00}};
3.14         For every v = V\0 evaluate:
3.15            D = D + max{0, d_{0v}};
3.16            Note: no d_{00} in this loop!
3.17         end;
3.18         Accept/refuse:
3.19            If D ≥ max{D(l'), D(l''), D_{Bonf}} + Δ, store triplet (l', l'', D) in selLoci.
3.20      Next (l', l'').
Output:   selLoci.
```

Lines 2.0-2.7 of the algorithm are used to find the binary classification rule with maximal attributable risk for a single SNP. In lines 3.0-3.17 we compute the maximal attributable risk for a grouping of genotype calls for a pair of SNPs. The number of the binary classification rules to search from may be reduced by grouping the genotype calls based on whether their attributable risk is negative or positive.

It will be appreciated that variations may be made to the algorithm, such as:

Variation 1: Best N-Hits.

We add triple (l',l'',D) to selLoci if selLoci stores less than N triplets or if it can replace a triplet $(l_1',l_1'',D_1)$ within selLoci with $D_1<D$.

Variation 2: Gain

We replace the acceptance conditions 3.18 and 3.19 with the following:

3.18 Accept/refuse:

3.19 If D≥max{D(l')+Δ(D(l')),D(l'')+Δ(D(l'')),D_{Bonf}}, store triplet (l',l'',D) in selLoci.

Here Δ (D) is a number defined such that:

$$BMD_0^a D(D+Δ(D)) ≤ BMD_0^a D(D)/F,$$

With F>1 is a gain factor, possibly chosen using Bonferroni $F=m^2$.

Algorithm 2: Screening for Optional Ratio of Risks

In another example, the binary classification rules may be related to ratios of risks derived from the contingency table.

```
Given a gain factor F > 1.
Initialise the set of selected loci: selLoci = { }
   For each locus l ∈ 𝓛 = {1, . . . m} find:
      the 2 × |V| contingency table:

n_{av} := ∑_{s∈S_n} 𝒥[g_l(s) ≡ v], where a = 0, 1 and v ∈ V.

the minimal p-value: p_l := min_{b, b: V→{0, 1}} BM (b ∘ g_l)/F,
         where F is a preselected constant > 1.
1.   For loop on pairs of loci (l', l'') ∈ 𝓛 × 𝓛;
2.      Load precomputed p-values p_{l'}, p_{l''} and marginal counts n_{av+} and n_{a+v'}
3.      Compute 2 × |V| × |V| contingency table n_{av'v''} := ∑_{s∈S_n} 𝒥[g_{l'}(s) ≡ v' & g_{l''}(s) ≡ v''], for a = 0, 1 and v', v'' ∈ V.
```

4. Find the sequence $\tau \mapsto (v'(\tau), v''(\tau))$ such that $\tau \to \frac{n_{1v'(\tau)v''(\tau)}}{n_{0v'(\tau)v''(\tau)}}$ is ascending.

5. Find minimal value $$p_{min} := \min_\tau BM\left(\sum_{i=0}^\tau n_{0v'(i)v''(i)}, \sum_{i=0}^\tau n_{1v'(i)v''(i)}\right).$$

6. If $p_{min} \leq \min\{p_{l'}, p_{l''}\}$, add triplet (l', l'', $p_{min}$) to selLoci.
7. Next (l', l'').
Output: selLoci In this case, the screening algorithm performed by the processing unit 110 detects the minimal p-value for ratio of risks of classification rule build on top genotype calls by each SNP pair.

As shown above, the binary classification rule is selected from multiple rules based on a statistical test (binomial margin test in this case) on the ratio of risks. The number of the binary classification rules from which the search is conducted is reduced based on the ordering shown in the algorithm.

It will be appreciated that variations may be made to the algorithm, such as:

Variation 1: Best N-Hits.
  Alternatively, we can replace the acceptance condition 5 by the following acceptance rule: We add triple (l'.l", $p_{min}$) to selLoci if selLoci stores less than N triplets or if it can replace a triplet within selLoci with larger p-value than $p_{min}$.

Variation 2: Multiple-Testing Correction
We replace the acceptance condition 6 with the following variation:

6. If $p_{min} \leq \min\{p_{l'}, p_{l''}, 1/F_2\}$, add triplet (l',l", $p_{min}$) to selLoci.
  where constant $F_2$ could be defined as the Bonferroni correction, $$F_2 = \binom{m}{2}$$

enforcing multiple testing correction.

Profiling

In another example, the processing unit 110 may profile the samples to determine one or more attributes of the samples, and subsequently use the attributes to determine the binary classification rules during the screening stage 220. The attributes may be related to one or more of distribution of genotype calls across the samples of the first trait and the samples of the second trait; distribution of loci position; and distribution of statistics The attributes may be related to the distribution of the samples. The distribution of risks for classification rules added on top of genotype calls can vary significantly from GWAS to GWAS. This can affect performance of epistasis detection system based on statistical filtering, as the acceptance threshold can be wrongly chosen, e.g. in auto immune diseases GWAS datasets, there are typically very significant interaction of SNPs with HLA region on human chromosome 6, driving p-values below $10^{-200}$. Such loci in combination with other "random" SNP, can proliferate p-values well in excess of Bonferroni threshold which is of order $\sim 10^{-14}$, so cut-off of that size results in acceptance of millions of pairs without evidence of interaction, i.e. evidence for improvement of pair over its components in isolation. This can drive the whole process of Stage 1 to standstill.

The profiling allows us to efficiently assess the distribution of risks in the data set. On that basis, we decide acceptance criteria for certain interesting regions. For example, in FIG. 5, we pre-select a region of interest (represented by 510 and 520), which translate to simple evaluation criteria, and then scan the data set to find the pairs satisfying this criteria. This restriction to the region of interest will require no statistics to evaluate in implementation of the statistical filtering stage 230, therefore simplifying significantly the computational task at hand.

Statistical Testing Stage 230

Referring to FIG. 2 again, the processing unit 110 then proceeds to perform statistical testing 230 on the candidate SNP-pairs that have passed the screening stage in step 220. This stage 230 involves evaluation of selected statistics are rigorously evaluated, ranking the candidates and selecting the most significant ones for further analysis. At this stage, the processing unit 110 also applies more computationally challenging filters (e.g. logistic regression) and cross checks against results in alternative studies.

Other steps performed during this stage 230 include:
  Computing full contingency tables for selected epistatic loci
  Computing full statistics
  Ranking candidates
  Selecting the most significant candidates
  Applying more computationally challenging filters or statistical tests, such as using binomial margins, logistic regression, Chi-square test and Fisher's exact test
  Performing replication validation by linking to alternative studies The statistical testing stage 230 may be interactive by providing an input interface for a user to provide input information relating to one or more statistical tests, such as using the interface in FIG. 5 as will be explained in more detail below in stage 250.

Analysis State 240

In step 240 in FIG. 2, the processing unit 110 performs biological-related analysis the possibly the hundreds of thousands of candidate pairs that have passed the rigorous statistical filtering stages in step 230.

For example, the candidate pairs are cross checked for participation in specific biological processes or pathways with the intention of identifying underlying biology driving the interaction. This involves condensing the reported interacting loci to interacting regions (accounting for the effect of linkage-disequilibrium), mapping these regions to genomic features such as genes, and correlating these putative interacting genes with known biological interaction data such as protein-protein interactions or gene regulatory networks. Finally, identification of the causal SNP participating in the interaction is attempted.

Interactions of LD-Blocks and Genes:

For example, the detected SNPs can be mapped to linkage disequilibrium (LD) blocks and thus allow to identify interactions on LD block level. Similarly, we can map SNP-markers to the nearest gene and determine interactions on gene levels. Both types of interactions can be readily visualised and analysed further.

Hub-SNPs:

In another example, for several diseases analysed to date we have observed SNPs abundantly involved in the interactions with many other SNPs, and we refer to them as hub-SNPs. Such effects could be for instance due to transe-QTL located on general transcription factors controlling expressions of many genes, but could be just modulations of a strong marginal SNP by "random" partners. Resolution of those issues requires additional analysis. Hub-SNP analysis could be useful for pathway and network construction.

Candidate SNP-pairs that pass the biological-related analysis will be marked as interacting SNP-pairs for presentation in step 250.

Results Presentation 250

Figure 5:
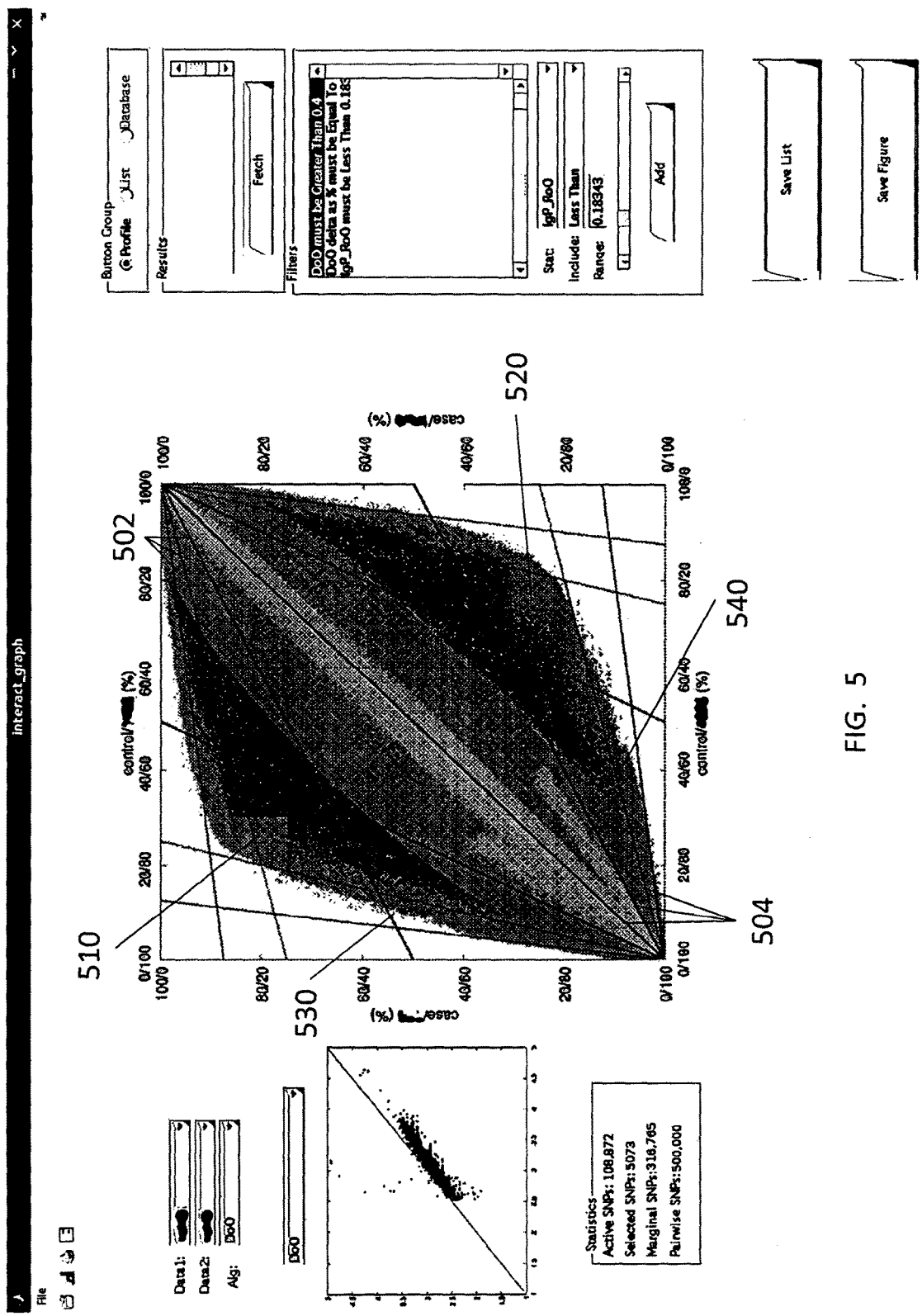
FIG. 5 is an example interface for results presentation and interactive filtering.

In step 250 in FIG. 2, the processing unit 110 presents the results on an graphical user interface, such as the one shown in FIG. 5.

In FIG. 5, we present scatter-plot comparing results of two GWA studies of disease discussed. We use a custom developed software tool, the Back-to-Back (B2B) browser.

The axes show empirical risks. The upper triangle shows the results for Study 1, and the lower one shows the results for Study 2.

The straight lines (purple 502 and black 504) mark different ratio of risks (RoR-2, RoR-4 and RoR-8). For each study (i.e. in each triangle), we show two sets of RoR values, one for protective alleles (purple, PR=control %/cases %, lines 502 from upper right hand corner at (100/0, 100/0)), one for disease alleles (black, DR=cases %/control %, lines 504 from lower left hand corner at (0/100,0/100)).

The light blue (labelled 530 and 540) background points show risks for significant binary epistasis rule; the yellow points show single SNP performance; the green points (labelled 510 and 520) show selected subsets in one study and its counterparts in the other study (ideally they are main axis mirror symmetry of each other). Note the extreme outlier mirroring each other. The dark blue show pre-filtered activated subsets. The parameter for selected pairs (green 510, 520) is shown in lower window. Graphs on left show selected summary statistics and scatter plots.

A number of other statistical contours could be overlaid as well. Alternatively, we could choose to display only a single study on the entire graph, using each half of the graph to show different statistics.

There are multiple ways for a user to input the kinds of SNPs they are searching for in an interactive manner. The most simple is to use a mouse to select those markers shown on the graph that are of interest. This may be useful to select a region that appears significant for a number of statistics or has a group of SNPs which cluster together.

Such an approach has been used in the image above to select a group of top discriminating SNPs from the first study. The visualisation has automatically plotted their counterparts in the second study (in green), and as their position on the graph is roughly symmetric, it again demonstrating potential replication. More complicated constraints can be entered on the right hand side of the tool, selecting the type of constraint desired, the threshold required and the direction of the threshold (greater, equal or less than). Again, the SNPs that pass the given constraints are highlighted in green on the center visualisation.

Moreover, the interactive filter is not restricted to the B2B plot shown above. Other visualisation (such as a heatmap of the SNPs indicating the regions of the chromosome that are interacting) can be used for the same task providing different views of how the selected SNPs are performing. FIG. 5 also demonstrates how such a visualisation can be integrated with other information. On the left-hand-side, there is an option for other related visualisation, showing the distribution of selected points in terms a selected statistic. The bottom part of the Figure shows a table of selected SNPs, suitable for export to Microsoft Excel or related spreadsheet software.

Figure 6:
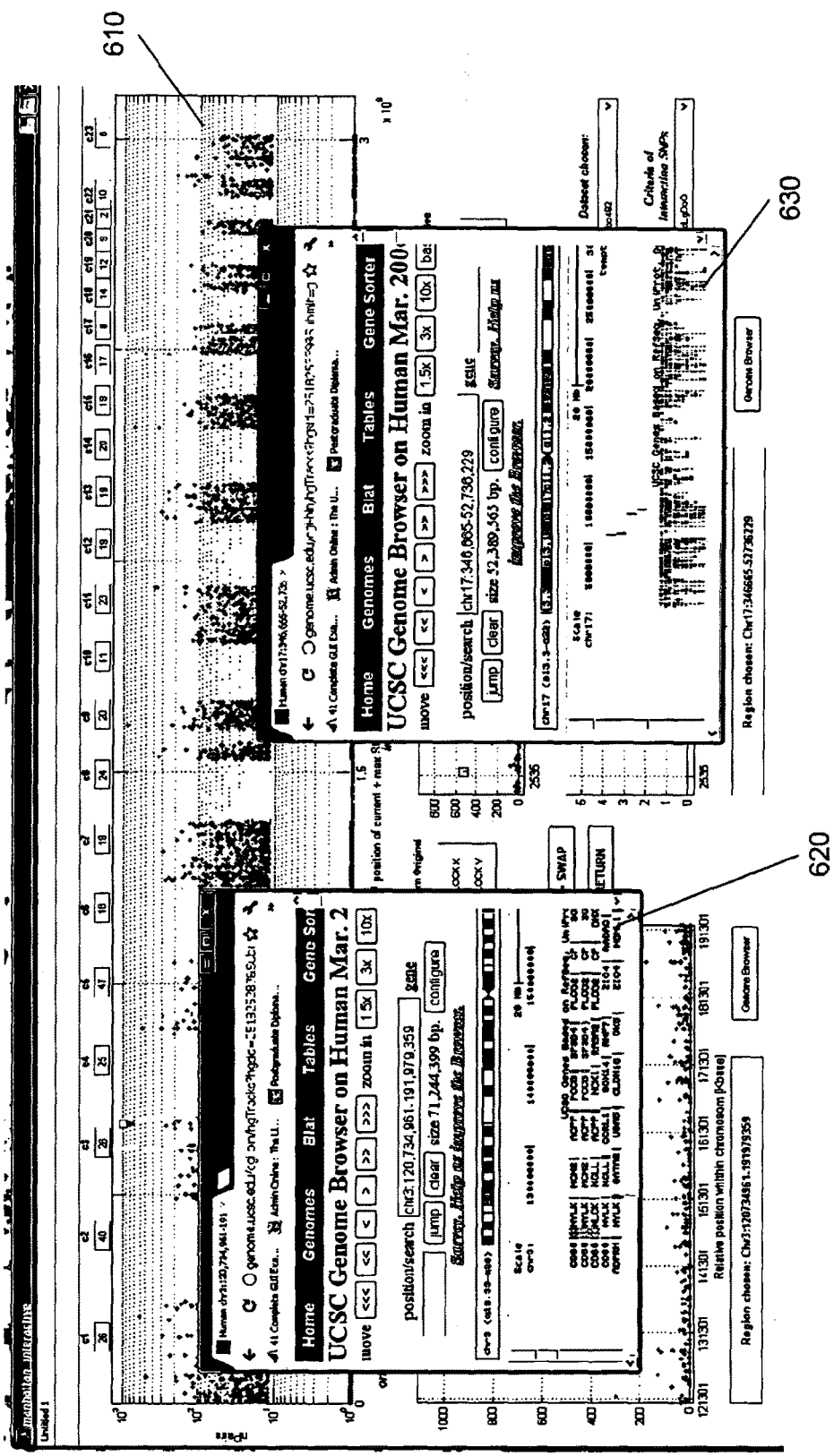
FIG. 6 is another example interface for results presentation.

Another example of the interface is shown in FIG. 6. The background 610 of this interface shows the "hub-SNPs", which are SNPs that are abundantly involved in the interactions with many other SNPs, found using one implementation of the method. An interesting hub-SNP can be selected and SNPs interacting with it will be highlighted. The bottom foreground windows are genome browsers, one 620 interrogating the selected hub-SNP and the other 630 showing a region of a selected SNP partners.

Figure 9:
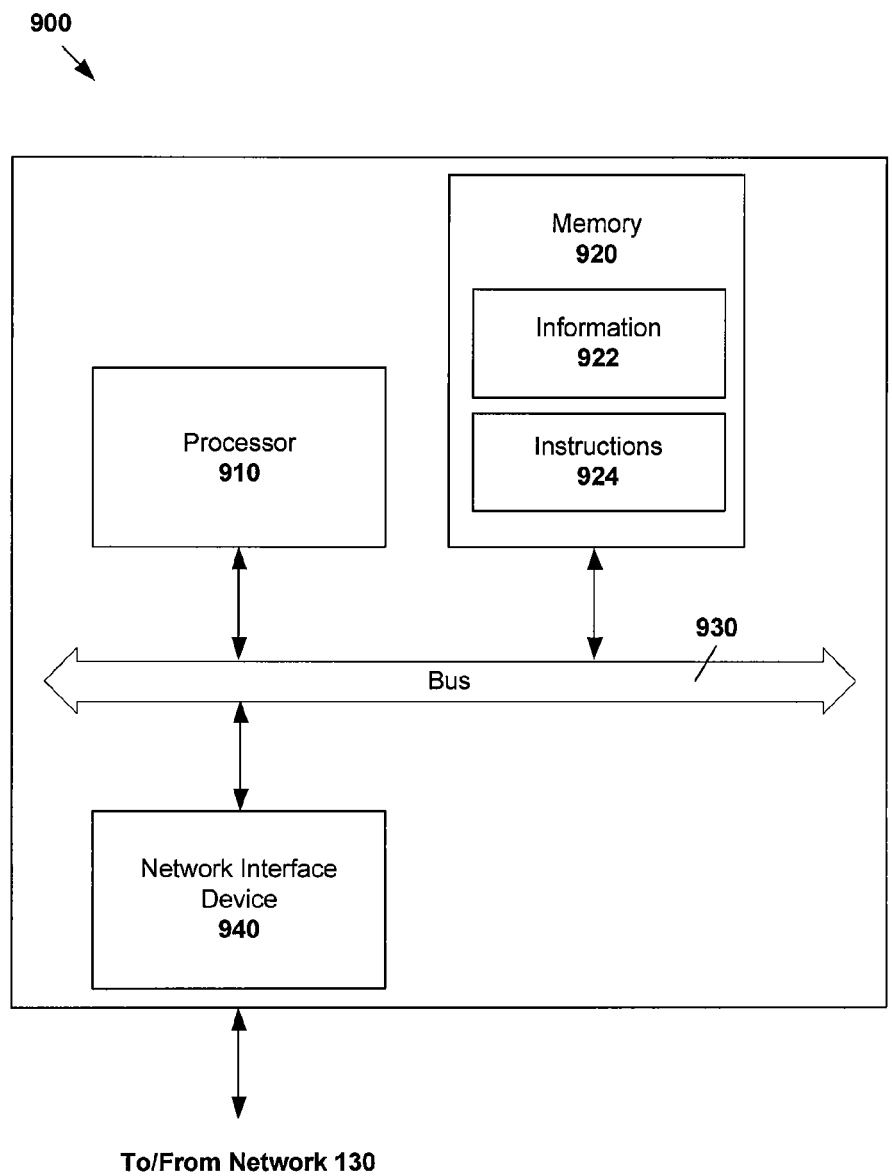
FIG. 9 is a schematic diagram of an example structure of a processing unit.

To visualise the candidate hub-SNPs as well as gene and LD block level associations, a visualisation tool was developed to allow interactive browsing of selected DNA loci. The software assists the researcher by providing independent zoom functions on each locus in the candidate pair, and integration with external sources of information. A screen shot of the visualisation interface is shown in FIG. 9.

Figure 7:
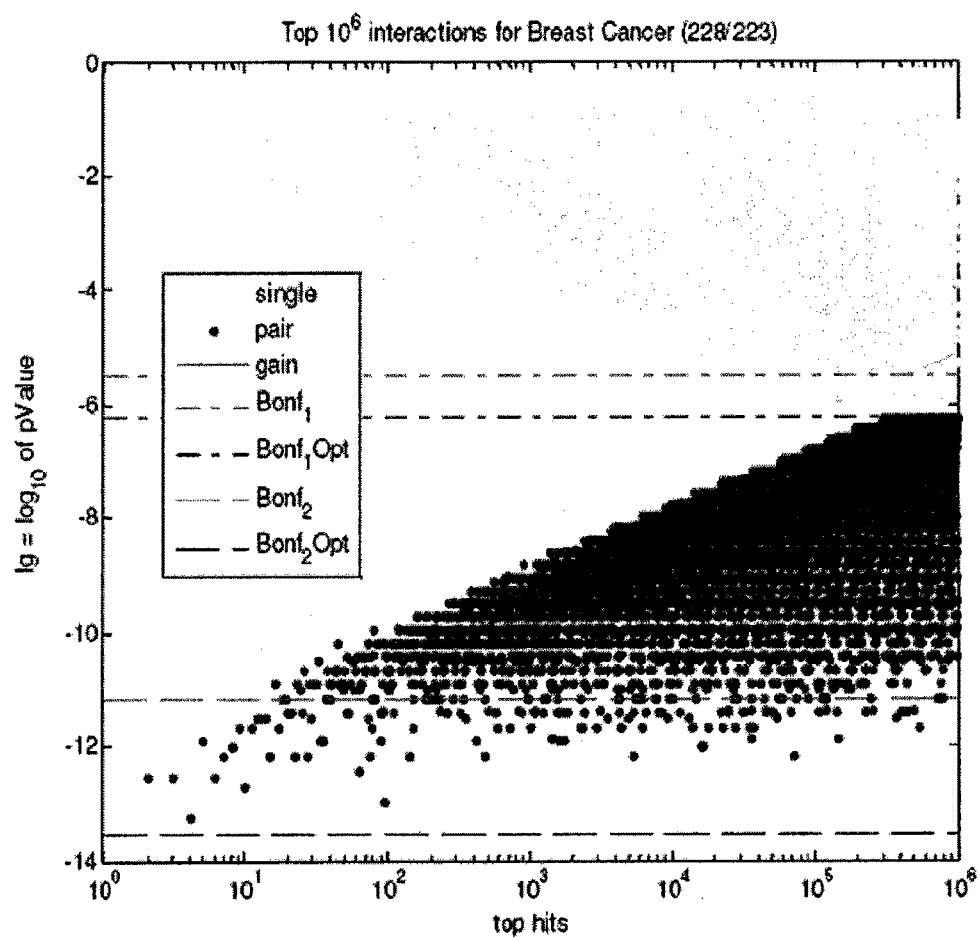
FIG. 7 is a chart showing example results for a case study of breast cancer.

The results of an analysis of a breast cancer GWAS are shown in FIG. 7, where we have found a wide range of putative epistasis interactions with a number of prominent hubs.

Comparison

The table in FIG. 8 shows are comparison between the method OPE (Optimal Pairwise Epistasis) performed by the processing unit 110, and other existing methods such as PLINK, MDR, BOOST and GBOOST.

For example, row 4 shows a comparison for 2-way interaction for the forthcoming case microarrays of 5 million SNPs. There is a massive difference in time between Column 2 (Baseline) and the last column, GPU cloud. The computational time factor here is massive. The gains are due to a combination of factors, which will be discussed below.

(a) Timing Comparison

TABLE 3

Comparison of timing results

| | Time for $n_{SNP} \times n_{samples}$ | | |
|---|---|---|---|
| Method | 0.5M × 5K | 5M × 10K | $n_{filters}$ |
| CPU Implementation | | | |
| GWIS | 4.6 hours | 42 days | 3 |
| GWIS | 2.7 hours | 22 days | 1 |
| BOOST | 30 hours* | 250 days | 1 |
| PLINK (FastEpi) | 6 months | 100 years | 1 |

TABLE 3-continued

Comparison of timing results

| Method | Time for $n_{SNP} \times n_{samples}$ | | $n_{filters}$ |
|---|---|---|---|
| | 0.5M × 5K | 5M × 10K | |
| GPU Implementation | | | |
| GWIS | 25 mins | 3.5 days | 1 |
| GWIS | 35 mins | 4.9 days | 3 |
| GBOOST | 130 mins* | 18 days | 1 |
| $MDR_{perm}$ | 15 years* | 2900 years | 1 |

Table 3 shows timings obtained from running GWIS (Genome Wide Interaction Search, which is an example implementation of the method in FIG. 2) and other algorithms over an average GWAS dataset (500,000 SNPs and 5,000 samples). Alongside this, we show estimates from extrapolating the timings to the larger sized datasets that are likely to be producing using new GWAS arrays that are currently under production. We tested a number of algorithms designed for use with CPU and GPU implementations. Timings were measured on a standard desktop PC with a quad-core, 3 GHz, 64 bit CPU and using a NVIDIA GTX 470 graphics card. CPU and GPU methods are considered separately due to their different hardware requirements.

In one example implementation, results show that the exhaustive evaluation of all possible SNP pairs is feasible on a standard desktop in reasonable time, with GWIS taking 3 hours for CPU and 25 minutes for GPU implementations. In the second column of the table, showing the timings extrapolated to larger GWAS datasets, we demonstrated it is still possible to exhaustively analyse all pairs using GWIS.

When compared to other methods we see that GWIS is 5× faster than BOOST, a recent method based on log-linear models. This speed up is due to a combination of reasons including; an efficient binary representation of the data, careful choice of statistical filters used, parallel processor work assignment and efficient recombination of parallel work products (described below), and careful optimisation of the implementation itself in order to best leverage the available hardware. It should be understood, however, that these example implementations are not essential, depending of the applications.

Experimental results have shown that exhaustively searching all SNP pairs can be represented in such a way that allows the problem to be easily decomposed resulting in an "embarrassingly parallelisable" task which is well suited to multiple CPUs and GPUs. The GPU method shows an 8× improvement in speed versus the CPU implementation. Our timing compares very favorably with many other algorithms for pairwise epistasis detection. In particular, the eCEO algorithm needed 9 hours of computing time on a 43 node cluster to exhaustively evaluate all pairs in a same size dataset using the "Chi Squared" $\chi^2$ statistic. We are accomplishing this on a single desktop PC in a few minutes or a few hours, depending on whether an appropriate graphics card is available. The FastEpistasis algorithm also uses parallelism to speed up the processing of the task, reporting that 12 hours and 512 processors are required to compute all possible pairs on a dataset with 500K SNPs (though working with continuous rather than binary phenotypes).

(b) Algorithmic Gains

In some implementations, the algorithms we use are much simpler computationally than the algorithms in the baseline Column 2 in Table 3. Comparison of Column 2 against the single CPU implementation of our algorithms in Column 4 in Table 3 gives us some feel of that: we see reduction of computing time from 108 days to 6 hours, a gain of approximately 400 times, in a rough comparison of the two CPU implementations. In order to compare the Baseline implementation vs GPU, let us compare 100 days vs 5 mins on 500 GPU cores, which is 5×500 mins=2500 mins≈42 hours (1.8 days) on a single GPU core. This is 108/1.8≈51 times faster on a 'single core' GPU, than the Baseline algorithms in Column 2 and this has to be attributed directly to algorithmic improvements.

This implies the further major gains have to come from algorithm improvements, which reduce both cost and computational time.

Example Implementation(s)

Some aspects of our efficient implementation of algorithms for screening (stage 220 in FIG. 2).

(i) Binarisation of the problem: we have used systematic binary class rather than continuous regression. This gives us computational advantages, being compatible with the binary nature of computers. In particular, in the discussions relating to "binary classification rules" and "optimal binary genotype", it has been shown that a computationally efficient way of detecting optimal binary genotype, without the need of costly exhaustive search or fitting the regression model.

(ii) The computation of contingency table for interacting SNPs is generally the most computationally critical stage. Due to the binary representation, this is a single bit logical '&' (AND) operation. However, the direct implementation of this is computationally very costly due to the number of evaluations required. Our first remedy for this is to use matrix multiplication and evaluate millions of cases at the time. Algorithm $OPE_2$ is an example here: rather than computing individual cases, we compute |L'|×|L"|~10 million cases at the time. Modern CPUs are optimised for matrix multiplication, and we take advantage of it here. The gains are significant, even we use only a fraction of CPU potential: entries of our matrices are only 0's and 1's but CPU treats them as 32 or 64 bit integer words (we elaborate further improvements utilising this potential below). Our estimate is that this change to matrix multiplication gains us a factor of approximately 10 in computational efficiency. Sorting the primary data (SNPs) in descending order of merit also helps to minimise number of checks.

The methods developed here can be utilised to analysis of other GWAS datasets than those associated with disease. Examples of such applications are (i) detection of genes associated with traits of interest in human such as skin pigmentation; or (ii) genes associated with plant genotypes; or identification of DNA loci relevant to selective breeding of (iii) crops, or (iv) animals.

Processing Unit 110

The example method in FIG. 2 can be implemented by hardware, software or firmware or a combination thereof. Referring to FIG. 9, an example structure of a device 900 capable of acting as a processing unit 110 is shown.

The example device 900 includes a processor 910, a memory 920 and a network interface device 940 that communicate with each other via a bus 930. Information may be transmitted and received via the network interface device 940, which may include one or more logical or physical ports that connect the device 900 to another network device.

For example, the various methods, processes and functional units described herein may be implemented by the processor 910. The term 'processor' is to be interpreted broadly to include a CPU, processing unit, ASIC, logic unit, or programmable gate array etc. The processes, methods and functional units may all be performed by a single processor 910 or split between several processors (not shown in FIG. 9 for simplicity); reference in this disclosure or the claims to a 'processor' should thus be interpreted to mean 'one or more processors'.

Although one network interface device 940 is shown in FIG. 9, processes performed by the network interface device 940 may be split between several network interface devices. As such, reference in this disclosure to a 'network interface device' should be interpreted to mean 'one or more network interface devices".

The processes, methods and functional units may be implemented as machine-readable instructions executable by one or more processors, hardware logic circuitry of the one or more processors or a combination thereof. In the example in FIG. 9, the machine-readable instructions 924 are stored in the memory 920. Other information 922, such as contingency tables, and measures of association computed by the processing unit 110 may be stored in the memory 920, or remote data stores 120, 170 in FIG. 1.

Further, the processes, methods and functional units described in this disclosure may be implemented in the form of a computer program product. The computer program product is stored in a computer-readable storage medium and comprises a plurality of computer-readable instructions for making a device 900 implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

It should also be understood that, unless specifically stated otherwise as apparent from the following discussion, it is appreciated that throughout the description, discussions utilizing terms such as "classifying", "constructing", "receiving", "processing", "retrieving", "selecting", "calculating", "determining", "displaying" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices. Unless the context clearly requires otherwise, words using singular or plural number also include the plural or singular number respectively.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A computer-implemented method for detecting interacting DNA loci, the method comprising:
    (a) constructing, by a processing unit, a contingency table for each of at least 500,000 putative interacting DNA loci from each of at least 5,000 samples of each of a first trait and a second trait and storing the contingency table on computer memory,
    wherein, in the contingency table stored on computer memory and indicative of the samples of the first trait and the samples of the second trait, the samples are each associated with one of a plurality of genotype calls each relating to an interaction between multiple DNA loci, and
    wherein the contingency table stored on the computer memory is indicative of frequencies of each genotype call in the samples of the first trait and in the samples of the second trait;
    (b) retrieving the contingency table stored on the computer memory and based on the contingency table, determining by the processing unit measures of association between the plurality of genotype calls and the first trait or second trait and storing the measures of association on the computer memory;
    (c) determining by the processing unit a reduced subset of binary classification rules for the DNA loci based on the measures of association, the binary classification rules classifying the plurality of genotype calls into (i) a first group of genotype calls that is statistically significantly associated with the first trait, and (ii) a second group of genotype calls that is statistically significantly associated with the second trait;
    (c1) determining by the processing unit statistical significance of each of the binary classification rules in the reduced set based on a statistical test based on the frequencies in the contingency table;
    (c2) selecting by the processing unit the binary classification rule that is most statistically significant in classifying the plurality of genotype calls; and
    (d) reporting by the processing unit identities of interacting DNA loci which pass an acceptance criteria on the statistical significance of the interaction.

2. The method of claim 1, wherein the measures of association include ratio of proportion values, wherein each value is determined as a ratio between (i) a first proportion of samples of the first trait being associated with one of the genotype calls and (ii) a second proportion of samples of the second trait being associated with the genotype call.

3. The method of claim 2, wherein the statistical test is a binomial margin test on the ratio of proportion values.

4. The method of claim 2, wherein selecting the binary classification rule to classify the plurality of genotype calls further comprises reducing the number of the binary classification rules based on descending ordering of the ratio of proportion values by determining a subset of genotype calls containing the top genotype calls of the ordering.

5. The method of claim 2, wherein the measures of association include difference of proportion values, wherein each value is determined as a difference between (i) a first proportion of samples of the first trait being associated with one of the genotype calls and (ii) a second proportion of samples of the second trait being associated with the one genotype call.

6. The method of claim 5, wherein the statistical test is a binomial margin test or maximum likelihood test on the difference of proportion values.

7. The method of claim 5, wherein selecting the binary classification rule to classify the plurality of genotype calls further comprises reducing the number of the binary classification rules by grouping the genotype calls based on whether their difference of proportion values are negative or positive.

8. The method of claim 1, further comprising:
performing steps (a), (b) and (c) on multiple sets of DNA loci; ranking the sets of DNA loci according to statistical significance of their association with the (i) first trait or (ii) second trait; and
based on the ranking, determine a list of sets of DNA loci that are most statistically significantly associated with the (i) first trait, or (ii) second trait.

9. The method of claim 8, wherein ranking the sets of DNA loci is based on a gain in association of the DNA loci as a set with the (i) first trait, or (ii) second trait compared to individual association of each DNA locus in the set with (i) first trait, or (ii) second trait.

10. The method of claim 8, further comprising performing one or more statistical tests on the sets of multiple DNA loci in the list to reduce the size of the list.

11. The method of claim 10, wherein the one or more statistical tests include one or more of logistic regression, chi-square test, and Fisher's exact test.

12. The method of claim 1, further comprising providing a graphical interface that includes a visual representation that compares measures of association of plural sets of multiple DNA loci.

13. The method of claim 12, further comprising providing an input interface to receive input information relating to one or more statistical tests, and updating the visual representation according to the input information.

14. The method of claim 1, further comprising profiling the samples to determine one or more attributes of the samples, and using the one or more attributes to determine the one or more binary classification rules in step (b).

15. The method of claim 14, wherein the one or more attributes are related to one or more of:
distribution of genotype calls across the samples of the first trait and the samples of the second trait;
distribution of loci position; and
distribution of statistics.

16. The method of claim 1, further comprising, for verification purposes, comparing genotype calls that are classified as statistically significantly associated with the first trait or second trait with data relating to a biological aspect of the samples.

17. The method of claim 16, wherein the biological aspect includes one or both of
association of the set of multiple DNA loci with a linkage-disequilibrium block and the method for detecting interacting DNA loci thereby including analyzing interaction on a linkage-disequilibrium block level and
association with a nearest gene and the method for detecting interacting DNA loci-thereby including analyzing interaction on a gene level.

18. The method of claim 1, wherein one or more of the genotype calls each relate to an interaction between multiple DNA loci and at least one environmental variable.

19. The method of claim 1, wherein:
the first trait is resistance to a disease, and the second trait is lack of resistance to the disease; or
the first trait is a resistance to a chemical, and the second trait is lack of resistance to the chemical; or
the first trait is a response to a drug treatment, and the second trait is a lack of response to the drug treatment.

20. A non-transitory computer readable medium with executable instructions stored thereon to cause a processing unit to perform the method according to claim 1.

21. A computer system for detecting interacting DNA loci associated with a disease or being healthy, the system comprising a processing unit and stored, executable instructions to cause the processing unit to:
(a) construct a contingency table for each of at least 500,000 putative interacting DNA loci from each of at least 5,000 samples of each of a first trait and a second trait and store the contingency table on computer memory,
wherein the contingency table stored on the computer memory indicative of the samples of the first trait and the samples of the second trait are each associated with one of a plurality of genotype calls each relating to an interaction between multiple DNA loci, and
wherein the contingency table stored on the computer memory is indicative of frequencies of each genotype call in the samples of the first trait and in the samples of the second trait;
(b) retrieve the contingency table stored on the computer memory and based on the contingency table, determine measures of association between the genotype calls, and the first trait or second trait and store the measures of association on the computer memory; and
(c) determine a reduced subset of binary classification rules for the DNA loci based on the measures of association, the binary classification rules classifying the genotype calls into (i) a first group of genotype calls that are statistically significantly associated with the first trait and (ii) a second group of genotype calls that are statistically significantly associated with the second trait;
(c1) determine statistical significance of each of the binary classification rules in the reduced set based on a statistical test based on the frequencies in the contingency table;
(c2) select the binary classification rule that is most statistically significant in classifying the plurality of genotype calls; and
(d) report identities of interacting DNA loci which pass an acceptance criteria on the statistical significance of the interaction.

* * * * *